(12) United States Patent
Pratt et al.

(10) Patent No.: US 12,734,287 B2
(45) Date of Patent: Sep. 15, 2026

(54) FLUID STORAGE CONTAINER

(71) Applicant: KCI Manufacturing Unlimited Company, Athlone (IE)

(72) Inventors: Benjamin A. Pratt, Bracknell (GB); Shannon C. Ingram, Saint Paul, MN (US); Thomas A. Edwards, Bracknell (GB)

(73) Assignee: KCI Manufacturing Unlimited Company, Westmeath (IE)

( * ) Notice: Subject to any disclaimer, the term of this patent is extended or adjusted under 35 U.S.C. 154(b) by 263 days.

(21) Appl. No.: 18/692,481

(22) PCT Filed: Aug. 23, 2022

(86) PCT No.: PCT/IB2022/057873
§ 371 (c)(1),
(2) Date: Mar. 15, 2024

(87) PCT Pub. No.: WO2023/042014
PCT Pub. Date: Mar. 23, 2023

(65) Prior Publication Data

US 2024/0424193 A1 Dec. 26, 2024

Related U.S. Application Data

(60) Provisional application No. 63/244,491, filed on Sep. 15, 2021.

(51) Int. Cl.
*A61M 1/00* (2006.01)

(52) U.S. Cl.
CPC .............. *A61M 1/98* (2021.05); *A61M 1/912* (2021.05); *A61M 1/94* (2021.05);
(Continued)

(58) Field of Classification Search
CPC .......... A61M 1/98; A61M 1/912; A61M 1/94; A61M 2205/3327; A61M 2205/3331;
(Continued)

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Rebecca E Eisenberg
*Assistant Examiner* — Brandon W. Levy

(57) ABSTRACT

Apparatuses, systems, and methods for optimizing fluid storage in a negative pressure therapy system are described. A fluid storage canister includes a first section, a second section, a fluid flow pathway, and a forced air module. The first section is fluidly coupled to a dressing and stores fluid, and the second section is fluidly coupled to a therapy unit and stores fluid. The fluid flow pathway is disposed between the first section and the second section. The forced air module generates a fluid flow through the fluid flow pathway.

17 Claims, 10 Drawing Sheets

(52) U.S. Cl.
CPC ............... *A61M 2205/3327* (2013.01); *A61M 2205/3331* (2013.01); *A61M 2205/36* (2013.01); *A61M 2205/8206* (2013.01)

(58) Field of Classification Search
CPC ...... A61M 2205/36; A61M 2205/8206; A61M 1/884; A61M 1/90; A61M 1/784; A61M 1/962; A61M 1/80; A61M 1/74; A61F 13/05
See application file for complete search history.

(56) References Cited

U.S. PATENT DOCUMENTS 2,632,443 A 3/1953 Lesher
2,682,873 A 7/1954 Evans et al.
2,910,763 A 11/1959 Lauterbach
2,969,057 A 1/1961 Simmons
3,066,672 A 12/1962 Crosby, Jr. et al.
3,367,332 A 2/1968 Groves
3,520,300 A 7/1970 Flower, Jr.
3,568,675 A 3/1971 Harvey
3,648,692 A 3/1972 Wheeler
3,682,180 A 8/1972 McFarlane
3,826,254 A 7/1974 Mellor
4,080,970 A 3/1978 Miller
4,096,853 A 6/1978 Weigand
4,139,004 A 2/1979 Gonzalez, Jr.
4,165,748 A 8/1979 Johnson
4,184,510 A 1/1980 Murry et al.
4,233,969 A 11/1980 Lock et al.
4,245,630 A 1/1981 Lloyd et al.
4,256,109 A 3/1981 Nichols
4,261,363 A 4/1981 Russo
4,275,721 A 6/1981 Olson
4,284,079 A 8/1981 Adair
4,297,995 A 11/1981 Golub
4,333,468 A 6/1982 Geist
4,373,519 A 2/1983 Errede et al.
4,382,441 A 5/1983 Svedman
4,392,853 A 7/1983 Muto
4,392,858 A 7/1983 George et al.
4,419,097 A 12/1983 Rowland
4,465,485 A 8/1984 Kashmer et al.
4,475,909 A 10/1984 Eisenberg
4,480,638 A 11/1984 Schmid
4,525,166 A 6/1985 Leclerc
4,525,374 A 6/1985 Vaillancourt
4,540,412 A 9/1985 Van Overloop
4,543,100 A 9/1985 Brodsky
4,548,202 A 10/1985 Duncan
4,551,139 A 11/1985 Plaas et al.
4,569,348 A 2/1986 Hasslinger
4,605,399 A 8/1986 Weston et al.
4,608,041 A 8/1986 Nielsen
4,640,688 A 2/1987 Hauser
4,655,754 A 4/1987 Richmond et al.
4,664,662 A 5/1987 Webster
4,710,165 A 12/1987 McNeil et al.
4,733,659 A 3/1988 Edenbaum et al.
4,743,232 A 5/1988 Kruger
4,758,220 A 7/1988 Sundblom et al.
4,787,888 A 11/1988 Fox
4,826,494 A 5/1989 Richmond et al.
4,838,883 A 6/1989 Matsuura
4,840,187 A 6/1989 Brazier
4,863,449 A 9/1989 Therriault et al.
4,872,450 A 10/1989 Austad
4,878,901 A 11/1989 Sachse
4,897,081 A 1/1990 Poirier et al.
4,906,233 A 3/1990 Moriuchi et al.
4,906,240 A 3/1990 Reed et al.
4,919,654 A 4/1990 Kalt
4,941,882 A 7/1990 Ward et al.
4,953,565 A 9/1990 Tachibana et al.
4,969,880 A 11/1990 Zamierowski
4,985,019 A 1/1991 Michelson
5,037,397 A 8/1991 Kalt et al.
5,086,170 A 2/1992 Luheshi et al.
5,092,858 A 3/1992 Benson et al.
5,100,396 A 3/1992 Zamierowski
5,134,994 A 8/1992 Say
5,149,331 A 9/1992 Ferdman et al.
5,167,613 A 12/1992 Karami et al.
5,176,663 A 1/1993 Svedman et al.
5,215,522 A 6/1993 Page et al.
5,232,453 A 8/1993 Plass et al.
5,261,893 A 11/1993 Zamierowski
5,278,100 A 1/1994 Doan et al.
5,279,550 A 1/1994 Habib et al.
5,298,015 A 3/1994 Komatsuzaki et al.
5,342,376 A 8/1994 Ruff
5,344,415 A 9/1994 DeBusk et al.
5,358,494 A 10/1994 Svedman
5,437,622 A 8/1995 Carion
5,437,651 A 8/1995 Todd et al.
5,527,293 A 6/1996 Zamierowski
5,549,584 A 8/1996 Gross
5,556,375 A 9/1996 Ewall
5,607,388 A 3/1997 Ewall
5,636,643 A 6/1997 Argenta et al.
5,645,081 A 7/1997 Argenta et al.
6,071,267 A 6/2000 Zamierowski
6,135,116 A 10/2000 Vogel et al.
6,241,747 B1 6/2001 Ruff
6,287,316 B1 9/2001 Agarwal et al.
6,345,623 B1 2/2002 Heaton et al.
6,488,643 B1 12/2002 Tumey et al.
6,493,568 B1 12/2002 Bell et al.
6,553,998 B2 4/2003 Heaton et al.
6,814,079 B2 11/2004 Heaton et al.
7,846,141 B2 12/2010 Weston
8,062,273 B2 11/2011 Weston
8,216,198 B2 7/2012 Heagle et al.
8,251,979 B2 8/2012 Malhi
8,257,327 B2 9/2012 Blott et al.
8,398,614 B2 3/2013 Blott et al.
8,449,509 B2 5/2013 Weston
8,529,548 B2 9/2013 Blott et al.
8,535,296 B2 9/2013 Blott et al.
8,551,060 B2 10/2013 Schuessler et al.
8,568,386 B2 10/2013 Malhi
8,679,081 B2 3/2014 Heagle et al.
8,834,451 B2 9/2014 Blott et al.
8,926,592 B2 1/2015 Blott et al.
9,017,302 B2 4/2015 Vitaris et al.
9,198,801 B2 12/2015 Weston
9,211,365 B2 12/2015 Weston
9,289,542 B2 3/2016 Blott et al.
2002/0077661 A1 6/2002 Saadat
2002/0115951 A1 8/2002 Norstrem et al.
2002/0120185 A1 8/2002 Johnson
2002/0143286 A1 10/2002 Tumey
2010/0042059 A1* 2/2010 Pratt ...................... A61M 1/96 700/282
2013/0053798 A1* 2/2013 Coulthard ............... A61M 1/73 604/319
2014/0163491 A1 6/2014 Schuessler et al.
2014/0276499 A1 9/2014 Locke et al.
2015/0080788 A1 3/2015 Blott et al.
2019/0175797 A1 6/2019 Locke et al.
2019/0201595 A1* 7/2019 Jardret .................. A61M 1/962

FOREIGN PATENT DOCUMENTS

AU 755496 B2 12/2002
CA 2005436 A1 6/1990
DE 2640413 A1 3/1978
DE 4306478 A1 9/1994
DE 29504378 U1 9/1995
EP 0100148 A1 2/1984
EP 117632 A2 9/1984
EP 161865 A2 11/1985
EP 358302 A2 3/1990
EP 1018967 A1 7/2000

(56) References Cited

FOREIGN PATENT DOCUMENTS

| | | | |
|---|---|---|---|
| GB | 692578 | A | 6/1953 |
| GB | 2195255 | A | 4/1988 |
| GB | 2197789 | A | 6/1988 |
| GB | 2220357 | A | 1/1990 |
| GB | 2235877 | A | 3/1991 |
| GB | 2329127 | A | 3/1999 |
| GB | 2333965 | A | 8/1999 |
| JP | 4129536 | B2 | 8/2008 |
| SG | 71559 | | 4/2002 |
| WO | 80/02182 | A1 | 10/1980 |
| WO | 8704626 | A1 | 8/1987 |
| WO | 90010424 | A1 | 9/1990 |
| WO | 93009727 | A1 | 5/1993 |
| WO | 94020041 | A1 | 9/1994 |
| WO | 9605873 | A1 | 2/1996 |
| WO | 9718007 | A1 | 5/1997 |
| WO | 9913793 | A1 | 3/1999 |
| WO | 2022195377 | A1 | 9/2022 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

(56) References Cited

OTHER PUBLICATIONS

International Search Report and Written Opinion for Corresponding Application No. PCT/IB2022/057873, mailed Jan. 23, 2023.

* cited by examiner

FLUID STORAGE CONTAINER

CROSS-REFERENCE TO RELATED APPLICATIONS

This application is a U.S. National Stage Entry of International Application No. PCT/IB2022/057873, filed Aug. 23, 2022, which claims the benefit of priority to U.S. Provisional Application No. 63/244,491, filed on Sep. 15, 2021, which is incorporated herein by reference in its entirety.

TECHNICAL FIELD

The invention set forth in the appended claims relates generally to tissue treatment systems and more particularly, but without limitation, to fluid storage canisters.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for fluid handling and storage in a negative-pressure therapy environment are set forth in the appended claims. Illustrative embodiments are also provided to enable a person skilled in the art to make and use the claimed subject matter.

For example, in some embodiments, a canister is described. The canister can include a first section configured to be fluidly coupled to a dressing and a second section configured to be fluidly coupled to a therapy unit, both the first section and the second section can be configured to store fluid. The canister can also include a fluid flow pathway disposed between the first section and the second section. The canister can further include a forced air module configured to generate a fluid flow through the fluid flow pathway.

Alternatively, other example embodiments describe a therapy system. The therapy system can include a dressing configured to be positioned adjacent to a tissue site and a canister. The canister can include a first section, a second section, a fluid flow pathway, and a forced air module. The first section can include a first outer wall, a first interior wall, and a first evaporative membrane. The first interior wall can be configured to be attached to the first outer wall and the first evaporative membrane can be coupled to a second side of the first interior wall. The second section can include a second outer wall, a second interior wall, and a second evaporative membrane. The second interior wall can be configured to be attached to the second outer wall and the second evaporative membrane can be coupled to a first side of the second interior wall. The fluid flow pathway can be disposed between the second side of the first interior wall and the first side of the second interior wall. The fluid flow pathway can comprise a first opening on a first end of the canister and a second opening on a second end of the canister. The forced air module can be configured to cover the first opening. The forced air module can include a removable plate and a forced air device. The forced air device can be coupled to an interior side of the removable plate and can be configured to direct a fluid flow through the fluid flow pathway to the second opening. The system can further include a therapy module including a negative pressure pump, a control board and a power source. The power source and the negative pressure pump can be coupled to the control board.

In some embodiments, the forced air module can include a second power source and a second control board. The second power source and the second control board can be coupled to the interior side of the removable plate adjacent to the forced air device. The forced air module can further include a power control. The power control can be configured to extend through the removable plate from an exterior side to the interior side. The power control can be configured to provide communication between a user and the control board. The power control can be configured to allow the user to start and stop the forced air device.

A method for fluid evaporation is also described herein. Some example embodiments include a dressing that can be positioned adjacent to a tissue site and a canister that can be coupled to the dressing. The canister can include a first section, a second section, a fluid flow pathway, and a forced air module. The first section can include a first outer wall, a first interior wall, and a first evaporative membrane. The first interior wall can be configured to be attached to the first outer wall and the first evaporative membrane can be coupled to a second side of the first interior wall. The second section can include a second outer wall, a second interior wall, and a second evaporative membrane. The second interior wall can be configured to be attached to the second outer wall and the second evaporative membrane can be coupled to a first side of the second interior wall. The fluid flow pathway can be disposed between the second side of the first interior wall and the first side of the second interior wall. The fluid flow pathway can comprise a first opening on a first end of the canister and a second opening on a second end of the canister. The forced air module can be configured to cover the first opening. The forced air module can include a removable plate and a forced air device. The forced air device can be coupled to an interior side of the removable plate and can be configured to direct a fluid flow through the fluid flow pathway to the second opening.

The canister can be connected to a therapy module that can comprise a power source, a negative pressure pump, and a control board. The negative pressure pump can be started and can draw the tissue site to a desired therapy pressure. The negative pressure pump can also draw fluids away from the tissue site. The fluids can be collected in the canister and the forced air module can be operated. The forced air device can be operated to direct a fluid flow through the fluid flow pathway and over the first evaporative membrane and the second evaporative membrane.

A method for fluid collection and disposal is also described herein. Some example embodiments include a dressing that can be positioned adjacent to a tissue site and a canister that can be coupled to the dressing. The canister can include a first section, a second section, a fluid flow pathway, and a forced air module. The first section can include a first outer wall, a first interior wall, and a first evaporative membrane. The first interior wall can be configured to be attached to the first outer wall and the first evaporative membrane can be coupled to a second side of the first interior wall. The second section includes a second outer wall, a second interior wall, and a second evaporative membrane. The second interior wall can be configured to be attached to the second outer wall and the second evaporative membrane can be coupled to a first side of the second interior wall. The fluid flow pathway can be disposed between the second side of the first interior wall and the first side of the second interior wall. The fluid flow pathway can comprise a first opening on a first end of the canister and a second opening on a second end of the canister. The forced air module can be configured to cover the first opening. The forced air module can include a removable plate and a forced air device. The forced air device can be coupled to an interior side of the removable plate and can be configured to direct a fluid flow through the fluid flow pathway to the second opening.

The canister can be connected to a therapy module that can comprise a power source, a negative pressure pump, and a control board. The negative pressure pump can be operated and can direct fluid from the tissue site to the canister. The fluid flow from the forced air device can be directed over the first and second evaporative membranes when the forced air device is turned on. The fluid flow can be configured to assist with fluid evaporation. The forced air device can be stopped if the canister is full and ready for disposal. When the canister is full, the forced air module can be removed from the canister by disconnecting the removable plate from the canister. The forced air module and the canister can then both be disposed of.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
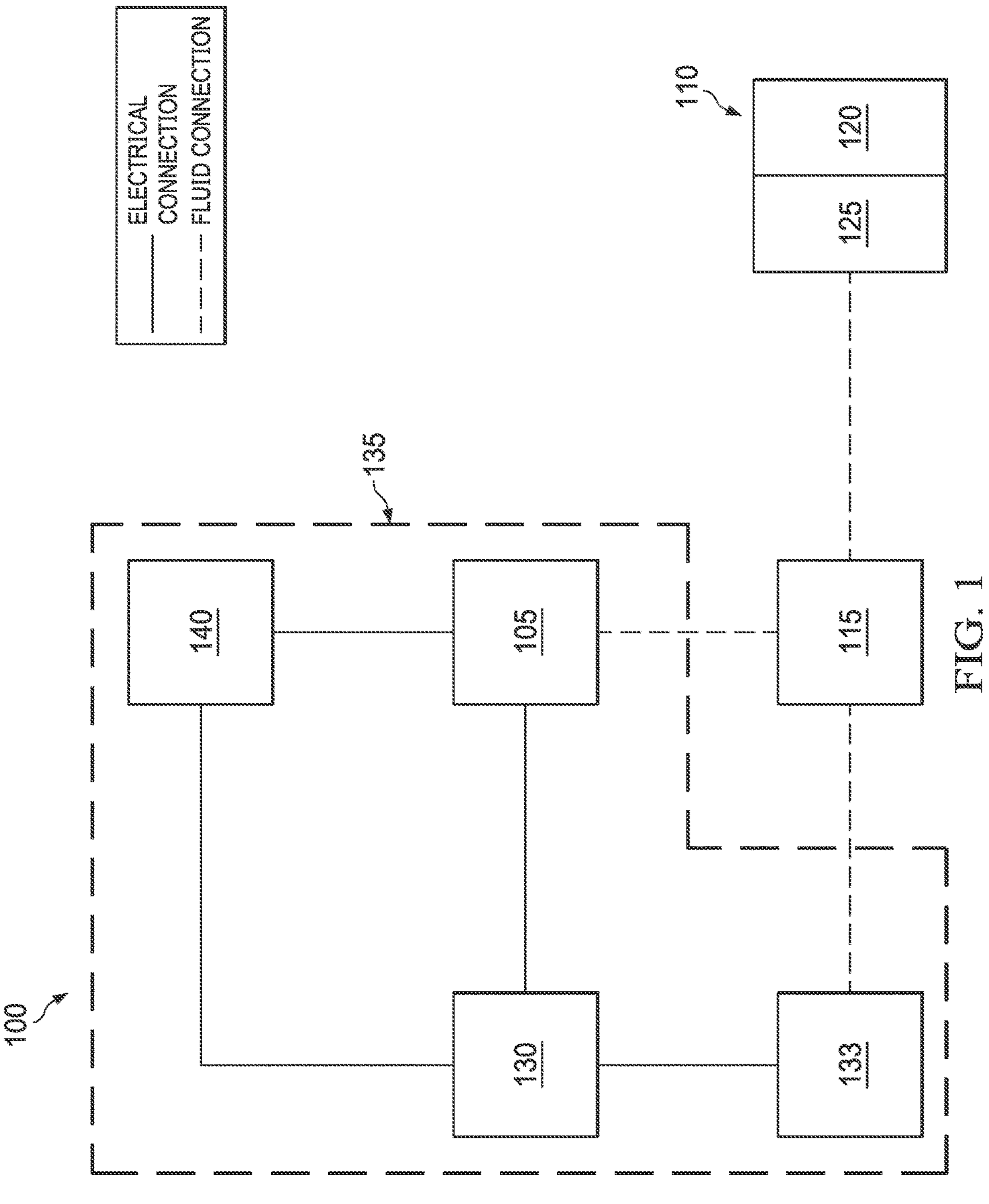
FIG. 1 is a functional block diagram of an example embodiment of a therapy system that can provide negative-pressure treatment in accordance with this specification.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a canister 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 133 and a second sensor 140 coupled to the controller 130.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130 and other components into a therapy unit 135.

In general, components of the therapy system 100 may be coupled directly or indirectly. For example, the negative-pressure source 105 may be directly coupled to the canister 115 and may be indirectly coupled to the dressing 110 through the canister 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a vacuum or a rough vacuum, between −5 mm Hg (−667 Pa) and −500 mm Hg (−66.7 kPa). Common therapeutic ranges are between −25 mm Hg (−6.7 kPa) and −300 mm Hg (−39.9 kPa).

The canister 115 is representative of a container, canister, pouch, or other storage component, which can be used to manage exudates and other fluids withdrawn from a tissue site. In many environments, a rigid canister may be preferred or required for collecting, storing, and disposing of fluids. In other environments, fluids may be properly disposed of without rigid canister storage, and a re-usable canister could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 133 and the second sensor 140, are generally known in the art as any apparatus operable to detect or measure a physical phenomenon or property, and generally provide a signal indicative of the phenomenon or property that is detected or measured. For example, the first sensor 133 and the second sensor 140 may be configured to measure one or more operating parameters of the therapy system 100. In some embodiments, the first sensor 133 may be a transducer configured to measure pressure in a pneumatic pathway and convert the measurement to a signal indicative of the pressure measured. In some embodiments, for example, the first sensor 133 may be a piezo-resistive strain gauge. The second sensor 140 may optionally measure operating parameters of the negative-pressure source 105, such as a voltage or current, in some embodiments. Preferably, the signals from the first sensor 133 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 120 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 120 may also vary according to needs of a prescribed therapy. The 25% compression load deflection of the tissue interface 120 may be at least 0.35 pounds per square inch, and the 65% compression load deflection may be at least 0.43 pounds per square inch. In some embodiments, the tensile strength of the tissue interface 120 may be at least 10 pounds per square inch. The tissue interface 120 may have a tear strength of at least 2.5 pounds per inch. In some embodiments, the tissue interface may be foam comprised of polyols such as polyester or polyether, isocyanate such as toluene diisocyanate, and polymerization modifiers such as amines and tin compounds. In some examples, the tissue interface 120 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 120 may also vary according to needs of a prescribed therapy. For example, the thickness of the tissue interface may be decreased to reduce tension on peripheral tissue. The thickness of the tissue interface 120 can also affect the conformability of the tissue interface 120. In some embodiments, a thickness in a range of about 5 millimeters to 10 millimeters may be suitable.

The tissue interface 120 may be either hydrophobic or hydrophilic. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

In some embodiments, the tissue interface 120 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S. A., Colombes, France; and Inspire 2301 and Inpsire 2327 polyurethane films, commercially available from Expopack Advanced Coatings, Wrexham, United Kingdom. In some embodiments, the cover 125 may comprise INSPIRE 2301 having an MVTR (upright cup technique) of 2600 $g/m^2/24$ hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in canister 115.

In some embodiments, the controller 130 may receive and process data from one or more sensors, such as the first sensor 133. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

Negative-pressure therapy has been repeatedly shown to be effective in the treatment of difficult to heal wounds. Manufacturers are designing current negative-pressure therapy systems to have a small footprint. A negative-pressure therapy system with a small footprint may reduce the cost of the device, the amount of manufacturing waste produced, and the amount of potentially biohazardous waste at the end of the lifecycle of the negative-pressure therapy system. A negative-pressure therapy system having a small footprint may also reduce patient impact during use of the negative-pressure therapy system. In addition to a reduction in size, negative-pressure therapy systems are also being designed for extended periods of patient use. In some cases the negative-pressure therapy system may be left in place for seven days or more. Often, a negative-pressure therapy system having a small footprint may not be available for use with extended placement dressing. The tissue site may produce exudate at a normal rate, and a small footprint negative-pressure therapy system may not have sufficient capacity to store the produced exudate without repeated stoppage of negative-pressure therapy to empty or replace a full canister. However, clinicians still desire to use the small footprint negative-pressure therapy systems due to the space savings and reduced patient impact. Many proposed solutions may fail to comply with existing disposal requirements and regulations that provide for separate disposal of electronic waste and medical waste. Therefore, a negative-pressure therapy system having a small footprint and capable of being left in place at a tissue site for an extended period is a long sought but unsolved solution in the art.

The canister 115 of the therapy system 100 may include features that enable evaporation of liquids received inside the canister 115. By enabling evaporation, the canister 115 may process more liquids than the canister 115 can physically retain during a given time period. The canister 115 may also enable independent disposal of different elements of the canister 115. For example, the canister 115 may have separable electronic components that permit disposal of the electronic components separately from remaining components of the canister 115. The figures may illustrate exemplary embodiments of the canister 115; however, other exemplary canisters may have other sizes, shapes, and/or configurations that fall within the scope of the described and illustrated embodiments.

Figure 2:
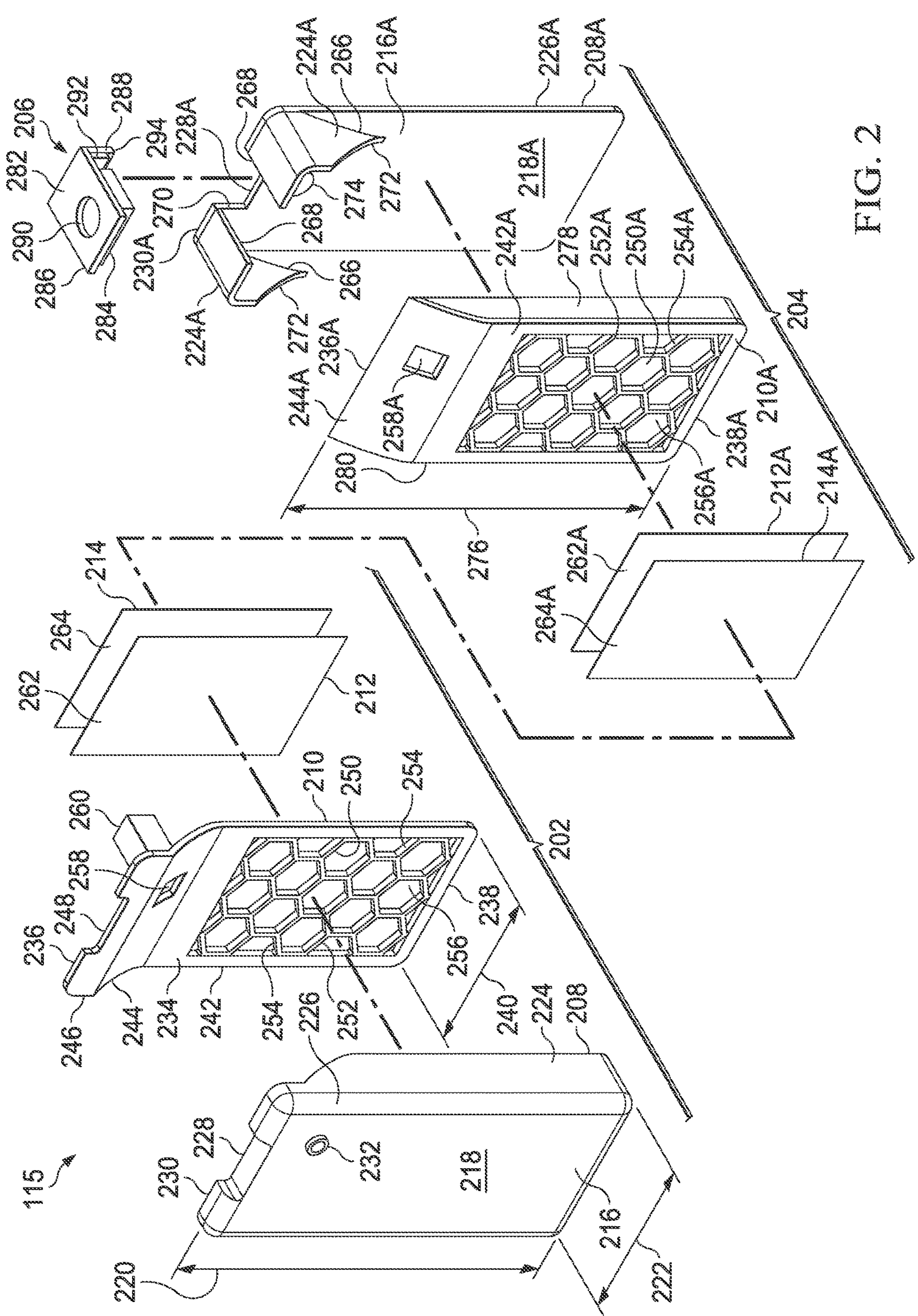
FIG. 2 is an exploded view of a canister that may be used with the therapy system of FIG. 1.

FIG. 2 is an exploded view illustrating details that may be associated with some embodiments of the canister 115 of the therapy system 100. In some embodiments, the canister 115 may comprise a first section, such as a first canister section 202, and a second section, such as a second canister section 204, both being configured to store fluid. The first canister section 202 may be fluidly connected to a dressing, such as the dressing 110. And the second canister section 204 may be configured to be fluidly connected to a negative-pressure source, such as the negative-pressure source 105. The canister 115 may further comprise a forced air module, such as a forced air module 206, and a fluid flow pathway. The fluid flow pathway may be disposed between the first canister section 202 and the second canister section 204. The fluid flow pathway may be configured to allow transmission of evaporated fluids from the canister 115 to the ambient environment.

The first canister section 202 may comprise an outer wall, an exterior wall, or a first outer section 208, a carrier or a first filter carrier 210, a distribution layer or a first nonwoven layer 212, and an evaporative layer or a first evaporative layer 214. In some embodiments, the first outer section 208 may have a substantially rectangular base 216. In other embodiments, the base 216 may be circular, triangular, ovular, or amorphous in shape. The base 216 may have a first surface 218 and a second surface opposite the first surface 218, a length 220, and a width 222 perpendicular to the length 220. In some embodiments, the length 220 may be greater than the width 222. In other embodiments, the length 220 may be substantially equal to the width 222.

The first outer section 208 may further have one or more projections or panels 224. In some embodiments, the one or more panels 224 may be coupled to a periphery or exterior edge 226 of the base 216. In some embodiments, the exterior edge 226 may be a joint of the one or more panels 224 and the base 216 and comprise a chamfered or beveled edge. In other embodiments, the exterior edge 226 may comprise a vertex of a perpendicular angle between the one or more panels 224 and the base 216. In some embodiments, a receiver or a notch 228 can be formed in an end 230. In some embodiments, the notch 228 extends through the base 216 from the first surface 218 to the second surface. The notch 228 may be positioned proximate a center of the width 222. In other embodiments, the notch 228 may not be centered on the width 222. In some embodiments, the notch 228 may have a width less than the width 222.

The one or more panels 224 may extend from and be perpendicular to the second surface of the base 216. In some embodiments, a panel 224 of the one or more panels 224 may extend from each edge of the base 216. In the illustrative embodiment, the end 230 is free of any panels 224. Each panel 224 may have a height and a length. In some embodiments, the height of each panel 224 is substantially equal. In other embodiments, the height of each panel 224 may vary. In the illustrative embodiment, the base 216 may have an end opposite the end 230, and two side surfaces extending from the end 230 to the end opposite the end 230. Each side surface may have a panel 224 extending from the end opposite the end 230 toward the end 230. In some embodiments, the panels 224 coupled to the side surfaces have a length less than the length 220 and may taper from the height of the panel 224 to the base 216 proximate the end 230.

A fluid connection point or a fluid inlet 232 can be disposed in the first outer section 208. In some embodiments, the fluid inlet 232 may provide fluid communication across the base 216. In some embodiments, the fluid inlet 232 may be configured to fluidly couple the canister 115 to the dressing 110. For example, a fluid conductor may be coupled to the fluid inlet 232 and similarly coupled to the dressing 110 to fluidly couple the canister 115 to the dressing 110. In some embodiments, the fluid inlet 232 may be disposed proximate the end 230 of the base 216. In some embodiments, the fluid inlet 232 may be positioned proximate to one of the panels 224 of the base 216 that is parallel to the length 220. In other embodiments, the fluid inlet 232 may be disposed in other locations on the base 216.

The first filter carrier 210 may comprise a first surface 234 and a second surface opposite the first surface 234. The first filter carrier 210 may also have a first end 236 and a second end 238 opposite the first end 236. The first end 236 and the second end 238 may have a width 240. In some embodiments, the width 240 may be substantially the same as the width 222. In other embodiments, the width 240 may be less than the width 222. The first filter carrier 210 may further include side edges extending from the second end 238 to the first end 236. The side edges may define a profile that substantially aligns with a height profile of the panels 224.

The first surface 234 of the first filter carrier 210 may be facing the first outer section 208 and the second surface of the first filter carrier 210 may be facing the first nonwoven layer 212. The first filter carrier 210 may comprise a first portion 242, a second portion 244, and a third portion 246. The second end 238 may be an end of the first portion 242, and the first end 236 may be an end of the third portion 246. In some embodiments, the first portion 242 of the first filter carrier 210 may be positioned so that the first portion 242 is parallel to the second surface of the base 216. Similarly, the third portion 246 can be positioned to be parallel to both the first portion 242 and the second surface of the base 216. In some embodiments, the third portion 246 and the first portion 242 are offset from each other. For example, the plane of the third portion 246 may be offset from the plane of the first portion 242 by a distance that is perpendicular to both the first portion 242 and the third portion 246. In some embodiments, the second portion 244 may couple the first portion 242 to the third portion 246. A first end of the second portion 244 may couple to an end of the first portion 242 opposite the second end 238. A second end of the second portion 244 may couple to an end of the third portion 246 opposite the first end 236. Both the first end and the second end may be coupled to their respective portion at a non-perpendicular angle to the respective portion.

In some embodiments, a receiver or a notch 248 can be formed in the first end 236. In some embodiments, the notch 248 extends through the first filter carrier 210 from the first surface 234 to the second surface. The notch 248 may be positioned proximate to a center of the width 240. In other embodiments, the notch 248 may not be centered on the width 240. In some embodiments, the notch 248 may have a width less than the width 240. In some embodiments, the notch 248 may be aligned with the notch 228 of the first outer section 208.

The first portion 242 may have a periphery or a peripheral portion, such as a first filter boundary 252 surrounding and defining an opening 250. In some embodiments, the opening 250 can comprise a substantial portion of the first portion 242. For example, the opening 250 may comprise greater than 50% of the surface area of the first portion 242. In some embodiments, the opening 250 may comprise about 50% to about 70% of the surface area of the first portion 242. In other embodiments, the opening 250 may be about 90% or greater of the surface area of the first portion 242. A first support framework, such as a first filter section 254 can be disposed in the opening 250.

The first filter section 254 can comprise a plurality of arms, beams, or braces extending across the opening 250. In some embodiments, the first filter section 254 forms a plurality of holes 256. Each hole 256 of the plurality of holes 256 may have a hexagonal shape. In some embodiments, each vertex of each hole 256 may be proximate to at least one vertex of an adjacent hole 256. In other embodiments, the plurality of holes 256 may comprise different sizes and shapes. The plurality of holes 256 may maintain all or substantially all of an open area through the opening 250 of the first portion 242 of the first filter section 254. The plurality of holes 256 of the first filter section 254 may be configured to allow fluid flow across the first filter section 254.

An opening 258 can be disposed in the second portion 244. The opening 258 can be configured to provide fluid communication across the first filter carrier 210 through the second portion 244. A fluid path 260 may be coupled to the opening 258 and may extend from the second side of the first filter carrier 210. The opening 258 may be off-center in the second portion 244. In some embodiments, the fluid path 260 may be configured to extend through the canister 115 to the second canister section 204. In other embodiments, the opening 258 and the fluid path 260 may be located at different locations on the first filter carrier 210 or there may be multiple fluid paths throughout the canister 115 to provide fluid communication between the first canister section 202 and the second canister section 204.

The first surface 234 of the first filter carrier 210 may be coupled to the one or more panels 224 and the end 230 of the first outer section 208. In other embodiments, the first filter carrier 210 may comprise a different size or shape but may still couple to the first outer section 208 to form the structure of the first canister section 202. In some embodiments, the first filter carrier 210 may be coupled to the first outer section 208 at one or more attachment points. In other embodiments, the first filter carrier 210 and the first outer section 208 may be coupled by compression gaskets, double sided adhesives, a weld, or any other suitable method of coupling to seal the first filter carrier 210 to the first outer section 208.

The first nonwoven layer 212 may have a first surface 262 and a second surface opposite the first surface 262. The first nonwoven layer 212 may be substantially the same shape as the first portion 242. The first surface 262 of the first nonwoven layer 212 may be configured to cover the opening 250 of the first filter carrier 210. The first surface 262 of the first nonwoven layer 212 may be coupled to the second surface of the first portion 242 along the first filter boundary 252. The first nonwoven layer 212 may contain additives that allow fluids from the canister 115 to be distributed to the first evaporative layer 214.

The first evaporative layer 214 may comprise a first surface 264 and a second surface opposite the first surface 264. The first evaporative layer 214 may comprise one or more evaporative membrane layers. The first evaporative layer 214 may be substantially the same shape as the first nonwoven layer 212. The first surface 264 of the first evaporative layer 214 may be configured to cover the second surface of the first nonwoven layer 212. In some embodiments, the first nonwoven layer 212 and the first evaporative layer 214 may be welded to the first filter carrier 210 along the first filter boundary 252. In other embodiments, the first nonwoven layer 212, the first evaporative layer 214, and the first filter carrier 210 may be coupled by other methods such as adhesives, compression gaskets, or other attachment methods.

The second canister section 204 may comprise an outer wall, an exterior wall, or a second outer section 208A, a second carrier or a second filter carrier 210A, a distribution layer or a second nonwoven layer 212A, and an evaporative layer or a second evaporative layer 214A. In some embodiments, the second outer section 208A may have a substantially rectangular base 216A. In other embodiments, the base 216A may be circular, triangular, ovular, or amorphous in shape. The base 216A may have a first surface 218A and a second surface opposite the first surface 218A. The second outer section 208A may have a length that is substantially the same as the length 220 of the first outer section 208. The second outer section 208A may have a width that is substantially the same as the width 222 of the first outer section 208.

In some embodiments, a receiver or a notch 228A may be formed in an end 230A. In some embodiments, the notch 228A extends through the base 216A from the first surface 218A to the second surface. The notch 228A may be positioned proximate to a center of the width. In other embodiments, the notch 228A may not be centered on the width. In some embodiments, the notch 228A may have a width less than the width 222. The second outer section 208A may further have one or more projections or extensions 224A. The extensions 224A may extend from corners formed between end 230A and sides 226A. The extensions 224A may extend towards the second filter carrier 210A. Each extension 224A may have a first edge 266 protruding from side 226A of the second outer section 208A. The first edge 266 may be closer to the end 230A than to an end of the second outer section 208A that is opposite the end 230A. Each extension 224A may have a second edge 268 protruding from the end 230A. Each second edge 268 may extend from corner 270 created on the end 230A where the notch 228A is formed. Each extension 224A may have a third edge 272 that may connect each first edge 266 to each second edge 268. The first edges 266 may be configured to couple the second outer section 208A to the second filter carrier 210A. The second edges 268 may be configured to couple the second outer section 208A to the forced air module 206. The third edges 272 may be configured to couple the second outer section 208A to the first filter carrier 210.

A negative-pressure inlet can be disposed in the second outer section 208A. In some embodiments, the negative-pressure inlet may be configured to fluidly couple the canister 115 to the negative-pressure source 105. For example, a fluid conductor may be coupled to the negative-pressure inlet and similarly coupled to the negative-pressure source 105 to fluidly couple the canister 115 to the negative-pressure source 105. In some embodiments, the negative-pressure inlet may be covered by a hydrophobic filter 274. The hydrophobic filter 274 may cover the negative-pressure inlet to ensure that liquids from the canister 115 cannot flow out of the canister 115 through the negative-pressure inlet. In some embodiments, the negative-pressure inlet is located proximate to the notch 279 of the second outer section 208A. In some embodiments, the negative-pressure inlet may be positioned proximate to the center of the width. In other embodiments, the negative-pressure inlet may not be centered on the width of the second outer section 208A.

The second filter carrier 210A may comprise a first surface 234A and a second surface opposite the first surface 234A. The second filter carrier 210A may also have a first end 236A and a second end 238A opposite the first end 236A. The first end 236A and the second end 238A may have a width that is substantially equal to width 240. In other embodiments, the width may be less than width 240 or may be less than width 222. The second filter carrier 210A may have a length 276 that is less than the length 220 of the first outer section 208.

The first surface 234A of the second filter carrier 210A may be facing the second nonwoven layer 212A and the second surface of the second filter carrier 210A may be facing the second outer section 208A. The second filter carrier 210A may comprise a first portion 242A and a second portion 244A. The second end 238A may be an end of the first portion 242A, and the first end 236A may be an end of the second portion 244A. In some embodiments, the first portion 242A of the second filter carrier 210A may be positioned so that the first portion 242A is parallel to the first surface 218A of the base 216A.

The second filter carrier 210A may further comprise one or more projections or panels 278. In some embodiments, the one or more panels 278 may be coupled to a periphery or exterior edge 280. In some embodiments, the exterior edge 280 may be a joint of the one or more panels 278 and the first portion 242A and the second portion 244A. In other embodiments, the exterior edge 280 may comprise a vertex of a perpendicular angle between the one or more panels 278 and the first portion 242A and the second portion 244A. The one or more panels 278 may extend from the second surface of the second filter carrier 210A. In some embodiments, a panel 278 or the one or more panels 278 may extend from each edge of the second filter carrier 210A. Each panel 278 may have a height and a length. In some embodiments, the height of each panel 278 is substantially equal. In other embodiments, the height of each panel 278 may vary.

The first portion 242A may have a periphery or a peripheral portion, such as a second filter boundary 252A. For example, the opening 250A may comprise greater than 50% of the surface area of the first portion 242A. In some embodiments, the opening 250A may comprise about 50% to about 70% of the surface area of the first portion 242A. In other embodiments, the opening 250A may be about 90% or greater of the surface area of the first portion 242A. A first support framework, such as a second filter section 254A can be disposed in the opening 250A.

The second filter section 254A can comprise a plurality of arms, beams, or braces extending across the opening 250A. In some embodiments, the second filter section 254A forms a plurality of holes 256A. Each hole 256A of the plurality of holes 256A may have a hexagonal shape. In some embodiments, each vertex of each hole 256A may be proximate to at least one vertex of an adjacent hole 256A. In other embodiments, the plurality of holes 256A may comprise different sizes and shapes. The plurality of holes 256A may maintain all or substantially all of the opening 250A of the first portion 242A of the second filter carrier 210A. The plurality of holes 256A of the second filter section 254A may be configured to allow fluid flow across the second filter section 254A.

An opening 258A can be disposed in the second portion 244A. The opening 258A can be configured to provide fluid communication across the second filter carrier 210A through the second portion 244A. The fluid path 260 may be coupled to the opening 258A. The opening 258A may be off-center in the second portion 244A. In other embodiments, the opening 258A may be located at different locations on the second filter carrier 210A or there may be multiple fluid paths throughout the canister 115 to provide fluid communication between the first canister section 202 and the second canister section 204.

The panels 278 of the second surface of the second filter carrier 210A may be coupled to the first surface 218A of the second outer section 208A. In other embodiments, the second filter carrier 210A may comprise a different size or shape but may still couple to the second outer section 208A to form the structure of the second canister section 204. In some embodiments, the second filter carrier 210A may be coupled to the second outer section at one or more attachment points. In other embodiments, the second filter carrier 210A may be coupled to the second outer section 208A by compression gaskets, double sided adhesives, a weld, or any other method of coupling to seal the second filter carrier 210A to the second outer section 208A.

The second nonwoven layer 212A may have a first surface 262A and a second surface opposite the first surface 262A. The second nonwoven layer 212A may be substantially the same shape as the first portion 242A. The second side of the second nonwoven layer 212A may be configured to cover the opening 250A of the second filter carrier 210A. The second side of the second nonwoven layer 212A may be coupled to the first side of the first portion 242A along the second filter boundary 252A. The second nonwoven layer 212A may contain additives that allow fluids from the canister 115 to be distributed to the second evaporative layer 214A.

The second evaporative layer 214A may have a first surface 264A and a second surface opposite the first surface 264A. The second evaporative layer 214A may comprise one or more evaporative membrane layers. The second evaporative layer 214A may be substantially the same size and shape as the second nonwoven layer 212A. The second surface of the second evaporative layer 214A may be configured to cover the first surface 262A of the second nonwoven layer 212A. In some embodiments, the second nonwoven layer 212A and the second evaporative layer 214A may be welded to the second filter carrier 210A along the second filter boundary 252A. In other embodiments, the second nonwoven layer 212A, the second evaporative layer 214A, and the second filter carrier 210A may be coupled by other methods such as adhesives, compression gaskets, or other attachment methods.

The forced air module 206 may comprise a removable plate 282 and a forced air device 284. The forced air device 284 may comprise a housing with a plurality of blades. In some embodiments, the forced air device 284 may be an axial fan, a centrifugal fan, a cross-flow fan, a bellows, a convective airflow device, an electrostatic airflow device, or another similar device configured to generate a fluid flow. The removable plate 282 may comprise a long face 286 and a short face 288. The long face 286 may have a greater surface area than the short face 288. The short face 288 may protrude from the long face 286 such that the long face 286 and the short face 288 are perpendicular. The removable plate 282 may comprise an interior side and an exterior side. There may be a hole 290 depending through the long face 286. The hole may allow the forced air device 284 to generate a fluid flow from the ambient environment outside the canister 115. In some embodiments, the hole 290 may be circular. In other embodiments, the hole 290 may be rectangular, ovular, triangular, or some other shape. The forced air device 284 may be coupled to the interior side of the removable plate 282 along the long face 286.

The forced air module 206 may further comprise electronic components such as an electronic component 292. The electronic component 292 may be proximate to the forced air device 284. The electronic component 292 may be attached to the long face 286 of the removable plate 282 between the forced air device 284 and the short face 288. The electronic component 292 may extend through the short face of the removable plate 282 from the exterior side to the interior side. The electronic component 292 may be configured to provide electric communication between the forced air module 206 and the controller 130 of the therapy unit 135. In some embodiments, the electronic component 292 may comprise pogo pins or another similar device.

The removable plate 282 may be configured to attach to the canister 115 at the first filter carrier 210 and the second outer section 208A. An end of the interior side of the long face 286 of the removable plate 282 proximate to the forced air device 284 and opposite the electronic component 292 may attach to the notch 248 of the first filter carrier 210. An edge 294 of the short face 288 of the removable plate 282 may attach to the notch 228A of the second outer section 208A. The removable plate 282 may be attached to the first filter carrier 210 and the second outer section 208A such that the forced air device 284 may be configured to sit between the third portion 246 of the first filter carrier 210 and the second portion 244A of the second filter carrier 210A. The removable plate 282 may be attached to the first filter carrier

210 and the second outer section 208A by any means that creates a sealed space while also allowing for the removable plate 282 to be removed from the canister 115 without compromising the remaining structure of the canister 115. In other embodiments, the removable plate 282 may have a different shape that may be configured to attach to the first filter carrier 210 and the second outer section 208A so that the canister 115 comprises a sealed space to store fluids.

The canister 115 may be formed by coupling the first canister section 202 to the second canister section 204. When the first canister section 202 and the second canister section 204 are combined, there may be a first end comprising a first opening and a second end comprising a second opening. The forced air module 206 may be coupled to the canister 115 at the first end to cover the first opening. When assembled, the canister 115 may comprise a sealed interior space and may be configured to house fluid and exudate drawn from the dressing 110. There may be a fluid flow pathway created between the first canister section 202 and the second canister section 204.

The first outer section 208, the first filter carrier 210, the second filter carrier 210A, the second outer section 208A, and the removable plate 282 may comprise a type of material having sufficient rigidity and structural integrity to withstand the reduced pressure required for negative-pressure treatment and to contain fluid therein. In some embodiments, the first outer section 208, the first filter carrier 210, the second filter carrier 210A, the second outer section 208A, and the removable plate 282 may comprise a clear rigid plastic such as ABS or TPU. Some exemplary materials of the first outer section 208, the first filter carrier 210, the second filter carrier 210A, the second outer section 208A, and the removable plate 282 are plastics, polymers, thermoplastics, metals, metal alloys, composition material, fiber-type materials, and other similar materials. The plastics described herein may be a substance or structure capable of being shaped or molded with or without the application of heat, a high polymer, usually synthetic, combined with other ingredients such as curatives, fillers, reinforcing agents, plasticizers, etc. Plastics can be formed or molded under heat and pressure in its raw state and machined to high dimensional accuracy, trimmed and finished in its hardened state. The thermoplastic type can be resoftened to its original condition by heat. In addition, the plastics may mean engineered plastics such as those that are capable of sustaining high levels of stress and are machinable and dimensionally stable. Some exemplary plastics are nylon, acetyls, polycarbonates, ABS resins, PPO/styrene, ISOPLAST 2530, TURLUX HS 2822, and polybutylene terephthalate. The thermoplastics described herein may be high polymers that soften when exposed to heat and return to their original condition when cooled to room temperature.

The first nonwoven layer 212 and the second nonwoven layer 212A may be comprised of a material of grade BK091620-11 having 158 gsm. In other embodiments, the first nonwoven layer 212 and the second nonwoven layer 212A may comprise Libeltex TDL2 or a similar material configured to encourage fluid flow from the canister 115 to the first evaporative layer 214 and the second evaporative layer 214A. In some embodiments, the first nonwoven layer 212 and the second nonwoven layer 212A may contain additives that help to distribute fluid and increase fluid contact with the first evaporative layer 214 and the second evaporative layer 214A. The coatings may be polar so as to attract water molecules. The coatings may include nitrogen, oxygen, or fluorine to enable hydrogen bonding which may quickly remove the hydrogen molecules from the canister 115 and distribute them to the first evaporative layer 214 and the second evaporative layer 214A and into the fluid flow pathway 408. In other embodiments, the coatings may include halogens such as chlorine and bromine. Other coatings may include metal compounds or polymers such as sodium, potassium, or calcium. In some embodiments, the coatings may be plasma coatings or may be a corona treatment designed to oxidize the first nonwoven layer 212 and the second nonwoven layer 212A to provide a polar coating. The coatings may be applied to the first surface 262 of the first nonwoven layer 212 and to the second surface of the second nonwoven layer 212A. In other embodiments, the coatings may be applied to the first surface 262 and the second surface of the first nonwoven layer 212 and to the first surface 262A and the second surface of the second nonwoven layer 212A.

The first evaporative layer 214 and the second evaporative layer 214A may be comprised of a high moisture vapor transmission rate (MVTR) film. The high MVTR film should have a MVTR of about 2000 to 5000 g/m$^2$/24 hrs in an upright cup test. The first evaporative layer 214 and the second evaporative layer 214A may be about 15 μm-50 μm thick. In some embodiments, the first evaporative layer 214 and the second evaporative layer 214A may each include two layers of high MVTR film that may each be about 20 μm thick. In other embodiments, the first evaporative layer 214 and the second evaporative layer 214A may each comprise one layer of high MVRT film that is about 40 μm-50 μm thick. In some embodiments, the high MVTR film may be BASF E1385A 12000 or COVESTRO Platilon U 250 μm. In other embodiments, the high MVTR film may be COVESTRO VPT 9121. The thickness of the COVESTRO VPT 9121 film may be about 15 μm to 100 μm. In some embodiments, the high MVTR films may act as filters that can prevent bacteria and viruses from escaping from the canister 115. The high MVTR films may be hydrophilic and may include polar elements such as nitrogen and oxygen. The hydrophilic nature and the polar elements of the high MVTR films may enable the diffusion of water molecules through the first evaporative layer 214 and the second evaporative layer 214A while hindering the diffusion of viruses or bacteria stored in the canister 115. More particularly, the high MVTR films may enable diffusion of particles that are smaller than about 0.50 nm, the high MVTR films may enable particles that are about 0.65 nm to enter the high MVTR films but they may not escape to the ambient environment surrounding the canister 115, and the high MVTR films may block particles greater than about 5 nm from escaping from the canister 115. Water molecules may be about 0.29 nm and may diffuse through the high MVTR films. Viruses are about 5 nm to about 100 nm and bacteria are about 200 nm to about 10,000 nm and may not diffuse through the high MVTR films.

In other embodiments, the canister 115 may have more than two canister sections and may have more than one fluid flow pathway. For example, the canister may comprise the first canister section 202, the second canister section 204, and a third canister section. The canister 115 may include the first evaporative layer 214, the second evaporative layer 214A, a third evaporative layer, and a fourth evaporative layer. The third evaporative layer and the fourth evaporative layer may line the second fluid flow pathway in a similar manner as how the first evaporative layer 214 and the second evaporative layer 214A line the fluid flow pathway between the first canister section 202 and the second canister section 204. Other embodiments of the canister 115 may include additional canister sections and additional fluid flow pathways in different locations to increase the amount of fluid that is evaporated out of the canister 115.

Figure 3:
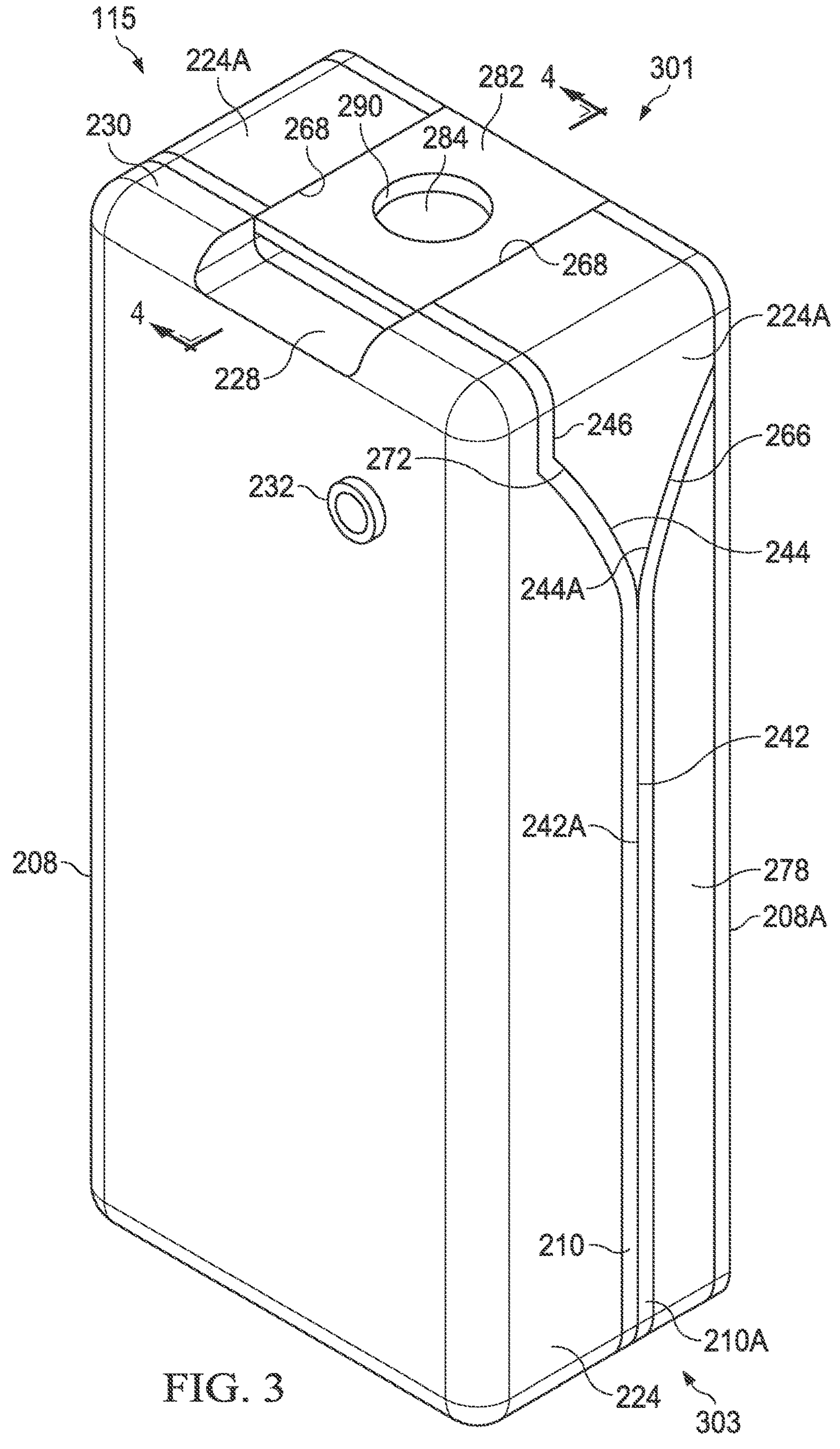
FIG. 3 is a perspective view of the canister of FIG. 2.

FIG. 3 is an assembled view of the canister 115 of FIG. 2. The first outer section 208, the second outer section 208A, the first filter carrier 210, the second filter carrier 210A, and the removable plate 282 seal the canister 115 so that fluid from the dressing 110 is contained in the canister 115. The removable plate 282 may be configured to cover the first opening on a first end 301 of the canister 115. The first end 301 may be opposite a second end 303 of the canister 115. The first filter carrier 210 may be coupled to the one or more panels 224 and the end 230 of the first outer section 208. The first portion 242 of the first filter carrier 210 may be coupled to the first portion 242A of the second filter carrier 210A. The base 216A of the second outer section 208A may be coupled to the panels 278 of the second filter carrier 210A. The extensions 224A of the second outer section 208A may be coupled to the second filter carrier 210A, the first filter carrier 210, and the removable plate 282. The first edge 266 may couple the second outer section 208A to the second portion 244A of the second filter carrier 210A. The second edge 268 may couple the second outer section 208A to the removable plate 282. The third edge 272 may couple the second outer section 208A to the second portion 244 and the third portion 246 of the second filter carrier 210A. The removable plate 282 may also be coupled to the first filter carrier 210 at the notch 248.

The canister 115 may be coupled to the dressing 110 at the fluid inlet 232. The fluid inlet 232 may be located on the first outer section 208 proximate to the end 230. The canister 115 may be coupled to the negative-pressure source 105 at the reduced pressure inlet of the second outer section 208A.

The hole 290 of the removable plate 282 may allow the forced air device 284 to generate a fluid flow from the ambient environment. The hole 290 and the forced air device 284 may be located between the first filter carrier 210 and the second filter carrier 210A. This positioning may allow the forced air device 284 to direct a fluid flow through the fluid flow pathway of the canister 115.

Figure 4:
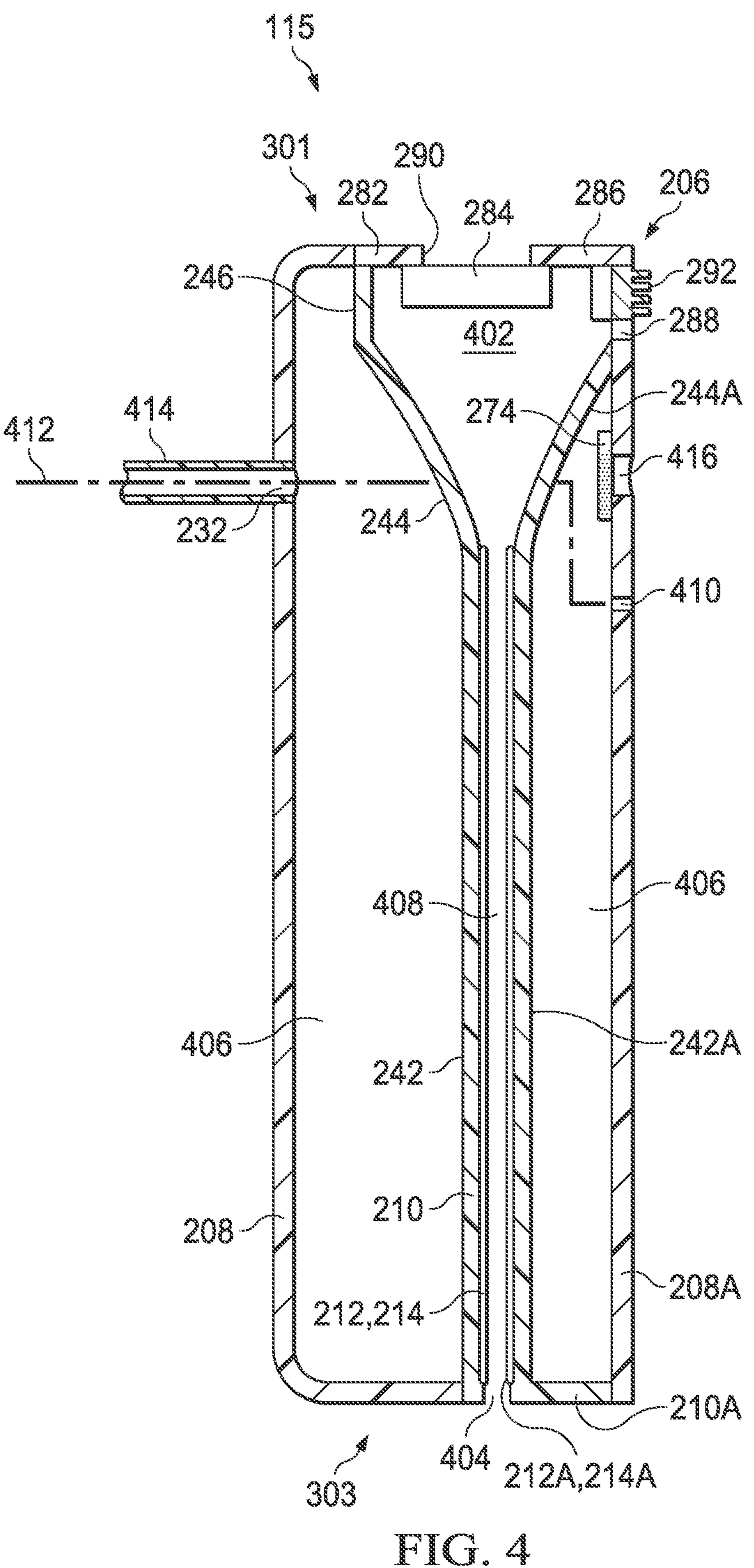
FIG. 4 is a cross-sectional view of the canister of FIG. 3 taken along line 4-4.

FIG. 4 is a cross sectional view of FIG. 3 taken along line 4-4 illustrating additional details that may be associated with some embodiments of the canister 115. The forced air module 206 may be configured to cover a first opening 402 at the first end 301 of the canister 115. The first opening 402 may be opposite a second opening 404 on the second end 303 of the canister 115. A portion of a sealed interior or fluid chamber 406 is disposed within the first canister section 202 between the first outer section 208 and the first filter carrier 210. Another portion of the fluid chamber 406 is disposed within the second canister section 204 between the second outer section 208A and the second filter carrier 210A. The first nonwoven layer 212 and the first evaporative layer 214 may be coupled to the first portion 242 of the first filter carrier 210. The second nonwoven layer 212A and the second evaporative layer 214A may be coupled to the first portion 242A of the second filter carrier 210A. The first evaporative layer 214 and the second evaporative layer 214A may be facing each other and may be lining a fluid flow pathway 408. The fluid flow pathway 408 may be fluidly isolated from the fluid chamber 406 of the canister 115. The fluid flow pathway 408 may extend from the first opening 402 at the first end 301 of the canister 115 to the second opening 404 at the second end 303 of the canister 115. The fluid flow pathway 408 may be wider at the first end 301 of the canister 115 and narrow to a thickness of around 2 mm between the first portion 242 of the second filter carrier 210A and the first portion 242A of the second filter carrier 210A.

The forced air device 284 may be configured to generate a fluid flow that may be directed through the fluid flow pathway 408. The fluid flow may flow from the forced air device 284 through the fluid flow pathway 408 to the second opening 404 at the second end 303 of the canister 115. The fluid flow may pass through the second opening 404 to the ambient environment surrounding the canister 115. In other embodiments, canister 115 may be constructed so that the fluid flow pathway 408 may open at a different side of the canister 115. In some embodiments, there may be a filter such as an odor filter disposed within the fluid flow pathway 408. In some embodiments the filter may be a charcoal filter. The filter may be disposed proximate to the second opening 404 at the second end 303 of the canister 115 and may be configured to filter the fluid flow passing through the fluid flow pathway 408 before the fluid flow reaches the ambient environment. In other embodiments, the filter may be disposed within the fluid chamber 406 of the canister. In some other embodiments, the forced air device 284 may be configured to generate a fluid flow through the fluid flow pathway 408 from the second end 303 to the first end 301. The forced air device 284 may be configured to pull the fluid flow through the fluid flow pathway 408 towards the forced air device 284. In the embodiments described herein, the forced air device 284 may operate at one speed or may be configured to operate at variable speeds.

During operation of the therapy system 100, the negative-pressure source 105 may draw fluid from the tissue site, generating a negative pressure in the sealed environment provided by the dressing 110. Fluid may be drawn from the dressing 110 and may flow into the canister 115 through the fluid inlet 232. Because the fluid inlet 232 is proximate to the end 230 of the first outer section 208, fluid may flow from the dressing 110 and fill the entire canister 115 before the fluid inside the canister reaches the fluid inlet 232. The fluid filling the canister 115 may flow through the opening 250 of the first filter carrier 210 and the opening 250A of the second filter carrier 210A to reach the first nonwoven layer 212, the first evaporative layer 214, the second nonwoven layer 212A, and the second evaporative layer 214A. The first evaporative layer 214 and the second evaporative layer 214A may allow evaporated liquids housed inside the canister 115 to escape to the ambient environment through the fluid flow pathway.

The forced air module 206 may be activated in response to a predetermined indicator. For example, in some embodiments, the therapy system 100 may operate the forced air device 284 if a level of fluid in the canister 115 reaches a predetermined level. In other embodiments, the therapy system 100 may operate the forced air device 284 in response to a predetermined pressure, humidity level, or another indicator. The forced air device 284 may be turned on and may direct a fluid flow through the fluid flow pathway 408 of the canister 115. The fluid flow from the forced air device 284 may assist in evaporation of any liquids that may be in contact with the first evaporative layer 214 and the second evaporative layer 214A of the canister 115.

The forced air module 206 may further comprise electronic components such as the electronic component 292. The electronic component 292 may extend through the short face 288 of the removable plate 282 from the exterior side to the interior side. The electronic component 292 may be configured to provide a communicative link between the forced air module 206 and the therapy unit 135. In some embodiments, the electronic component 292 may comprise pogo pins or another similar design. In some embodiments, the forced air module 206 may further include a heating device. The heating device may be configured to heat the fluid flow generated by the forced air device 284. By increasing the temperature of the fluid flow, the rate of evaporation in the canister 115 through the first evaporative layer 214 and the second evaporative layer 214A can be increased. In some embodiments, the heating device may be configured to heat the fluid flow to a temperature of about 38 degrees C. The upper limit of the fluid flow temperature may be around 38 degrees C. to protect a user from being burned by the heat generated by the heating device.

In some embodiments, the canister 115 may comprise a connection point 410. The connection point 410 may be configured to allow a sensor to extend along a sensor pathway 412 to from the therapy unit 135 to the canister 115. The sensor pathway 412 may extend from the canister 115 to the dressing 110 through the fluid inlet 232. In some embodiments, the sensor may be SENSAT.R.A.C.™ Technology used to facilitate communication from the therapy unit 135 to the dressing 110 along the sensor pathway 412. The sensor pathway 412 may be placed through a conduit 414 that is connected to the fluid inlet 232. The conduit 414 may be configured to couple to the dressing 110 and to deliver negative pressure from the therapy unit 135 to the dressing 110. The sensor pathway 412 may provide a feedback loop from the dressing 110 to the controller 130. The therapy unit 135 may also be connected to the canister 115 at a reduced pressure inlet 416. The reduced pressure inlet 416 may be covered by the hydrophobic filter 274. The reduced pressure inlet 416 may be configured to couple to the negative-pressure source 105 of the therapy unit 135.

Figure 5:
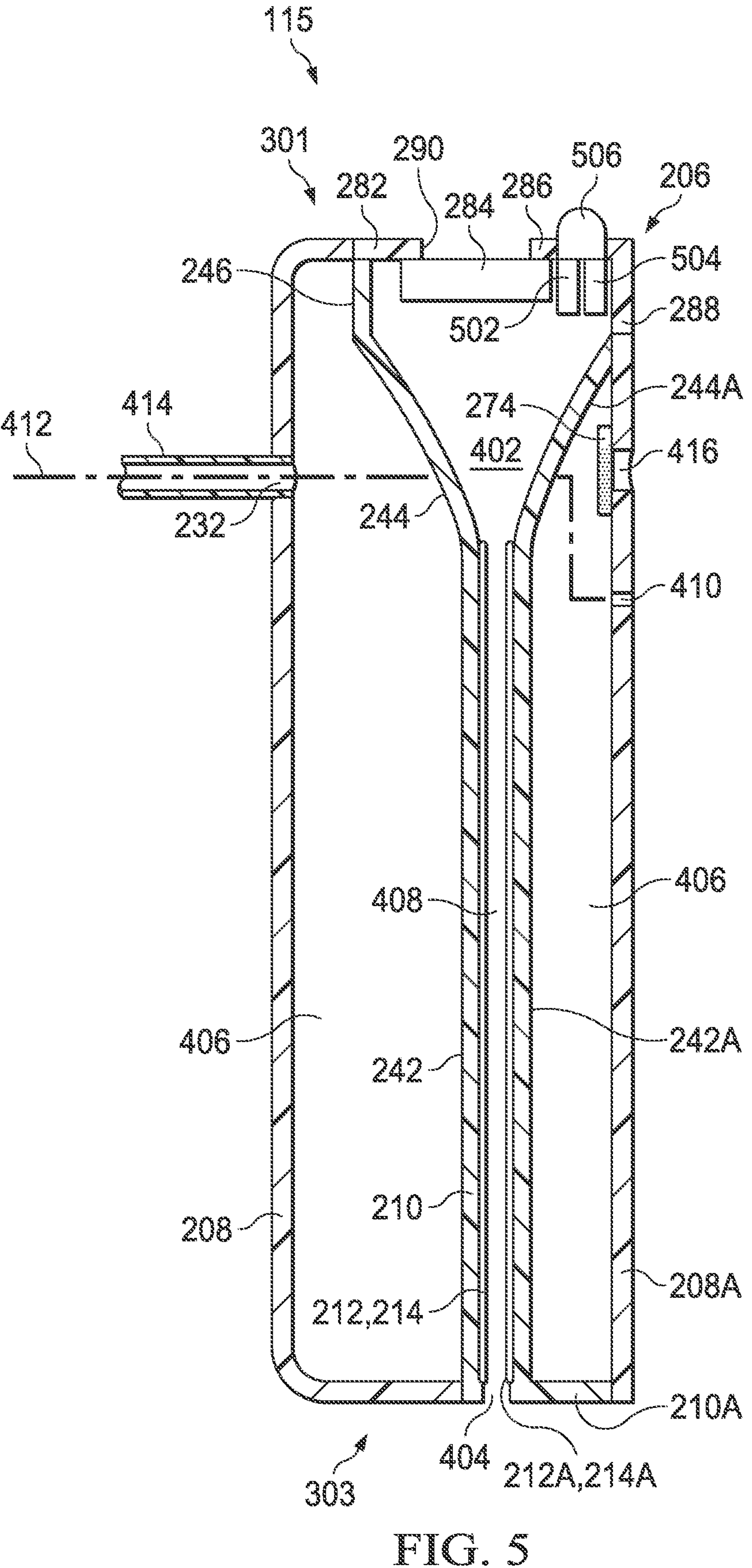
FIG. 5 is a cross-sectional view of the canister of FIG. 2 illustrating an example of a power control, a power source, and a control board that may be used with some embodiments.

FIG. 5 is a cross sectional view illustrating additional details that may be associated with some embodiments of the canister 115. In some embodiments, the forced air module 206 may also comprise a power source 502, a control board 504, a power control 506, and the forced air device 284. The control board 504 may be communicatively coupled to the forced air device 284 and the power source 502. In some embodiments, the control board 504 and the power source 502 may be electrically coupled. The power control 506 may be coupled to the power source 502 or coupled to both the power source 502 and the control board 504. The power source 502 and control board 504 may permit the forced air module 206 to operate without communication between the forced air module 206 and the therapy unit 135.

The power source 502 may comprise a single battery, multiple batteries, a solar power source, or another source of electric power. In some embodiments, the power source 502 may be rechargeable. In some embodiments, the forced air module 206 may be removed from the canister 115 and replaced with another forced air module 206 while the power source 502 is being replaced or being recharged. In other embodiments, the power source 502 may be configured to be charged without removing the forced air module 206 from the canister 115. In other embodiments, the forced air module 206 may be designed so that the power source 502 is configured to provide power to the forced air module 206 for about seven days or more without replacement or recharge.

The power control 506 may be coupled to the removable plate 282 and may be in communication for example, by electric communication or coupling to both the power source 502 and the control board 504. In some embodiments, the power control 506 may comprise a button that is configured to activate the power source 502 if the power control 506 is turned to an on position. The power control 506 may be configured to deactivate the power source 502 if the power control 506 is turned to an off position. The power control 506 may allow a patient or a health care provider to manually operate the forced air device 284. For example, a health care provider may operate the forced air device 284 in response to a level of fluid located inside the canister 115.

The forced air device 284 may be turned off until there is an optimal level of fluid stored in the canister 115. Prior to this optimal level of fluid, the forced air device 284 may not provide significant assistance in fluid evaporation and having the forced air device 284 turned on may unnecessarily degrade the battery life of the power source 502 of the forced air module 206. The optimal level of fluid for operation of the forced air device 284 may depend on the orientation of the canister 115. In some embodiments, the canister 115 is in a vertical orientation. In the vertical orientation, if there is any fluid in the canister 115, there will be at least minimal contact with at least one of the first evaporative layer 214 or the second evaporative layer 214A. Thus, when the canister 115 is in a vertical orientation, the forced air device 284 may be actuated if there is any fluid in the canister 115. In other embodiments, the canister 115 may be in a horizontal orientation. In a horizontal orientation, fluid located in the canister 115 may not come in contact with either the first evaporative layer 214 or the second evaporative layer 214A until the canister 115 contains a specific amount of fluid. For example, if the first evaporative layer 214 was located a quarter of the way from a base of a horizontally oriented canister 115, the canister 115 would need to be 25% full of fluid before the fluid would be in contact with the first evaporative layer 214. Thus, the forced air device 284 may not be turned on until the canister 115 is approaching about 25% capacity.

Figure 6:
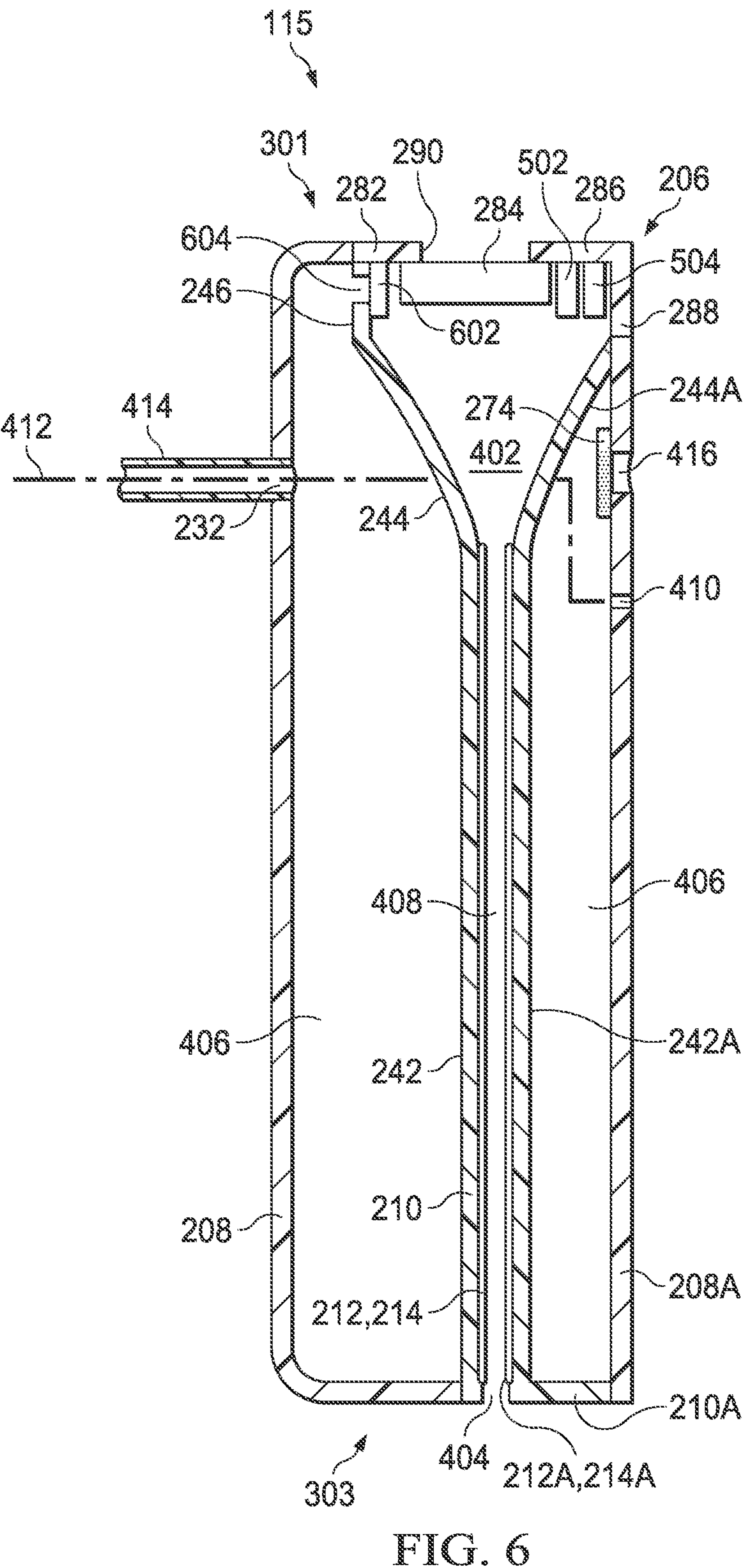
FIG. 6 is a cross-sectional view of the canister of FIG. 2 illustrating an example of a pressure sensor that may be used with some embodiments.

FIG. 6 is a cross sectional view illustrating additional details that may be associated with some embodiments of the canister 115. In some embodiments, the forced air module 206 may comprise the removable plate 282, the forced air device 284, the power source 502, and the control board 504. The canister 115 may comprise a pressure sensor 602. The pressure sensor 602 may communicate with the fluid chamber 406 through an opening 604. The opening 604 may be located through the third portion 246 of the first filter carrier 210. In other embodiments, the opening 604 may be at a different location in the canister 115 while allowing the pressure sensor 602 to communicate with the fluid chamber 406. The pressure sensor 602 may be configured to seal the fluid flow pathway 408 from any fluid passage across the pressure sensor 602.

The pressure sensor 602 may be configured to sense the pressure in the canister 115 to determine if negative pressure is being applied to the fluid chamber 406. In some embodiments, the pressure sensor 602 may be configured to control the operation of the forced air device 284. For example, the forced air device 284 may be operated if the pressure sensor 602 determines that negative pressure is being applied to the fluid chamber 406. If the pressure sensor 602 determines that negative pressure is no longer being applied to the fluid chamber 406 or that the pressure in the fluid chamber 406 has fallen below a predetermined level or a threshold pressure, the forced air device 284 may be turned off. In some embodiments, the forced air device 284 may remain on for a predetermined amount of time after the pressure sensor 602 detects that there is no longer negative pressure being applied to the fluid chamber 406. The predetermined time may be about 10 minutes. During operation, the pressure sensor 602 may detect negative pressure in the fluid chamber 406. In response, the pressure sensor 602 may generate and communicate a signal to the control board 504, which may operate the forced air device 284. If the negative pressure decreases, the pressure sensor 602 may generate a signal indicative of the change in negative pressure. If the negative pressure falls below the predetermined level for about 10 minutes, the control board 504 may operate the forced air device 284 for an additional 2 minutes to 15 minutes. After the additional about 2 minutes to about 15 minutes, the control board 504 may turn off the forced air device 284.

Figure 7:
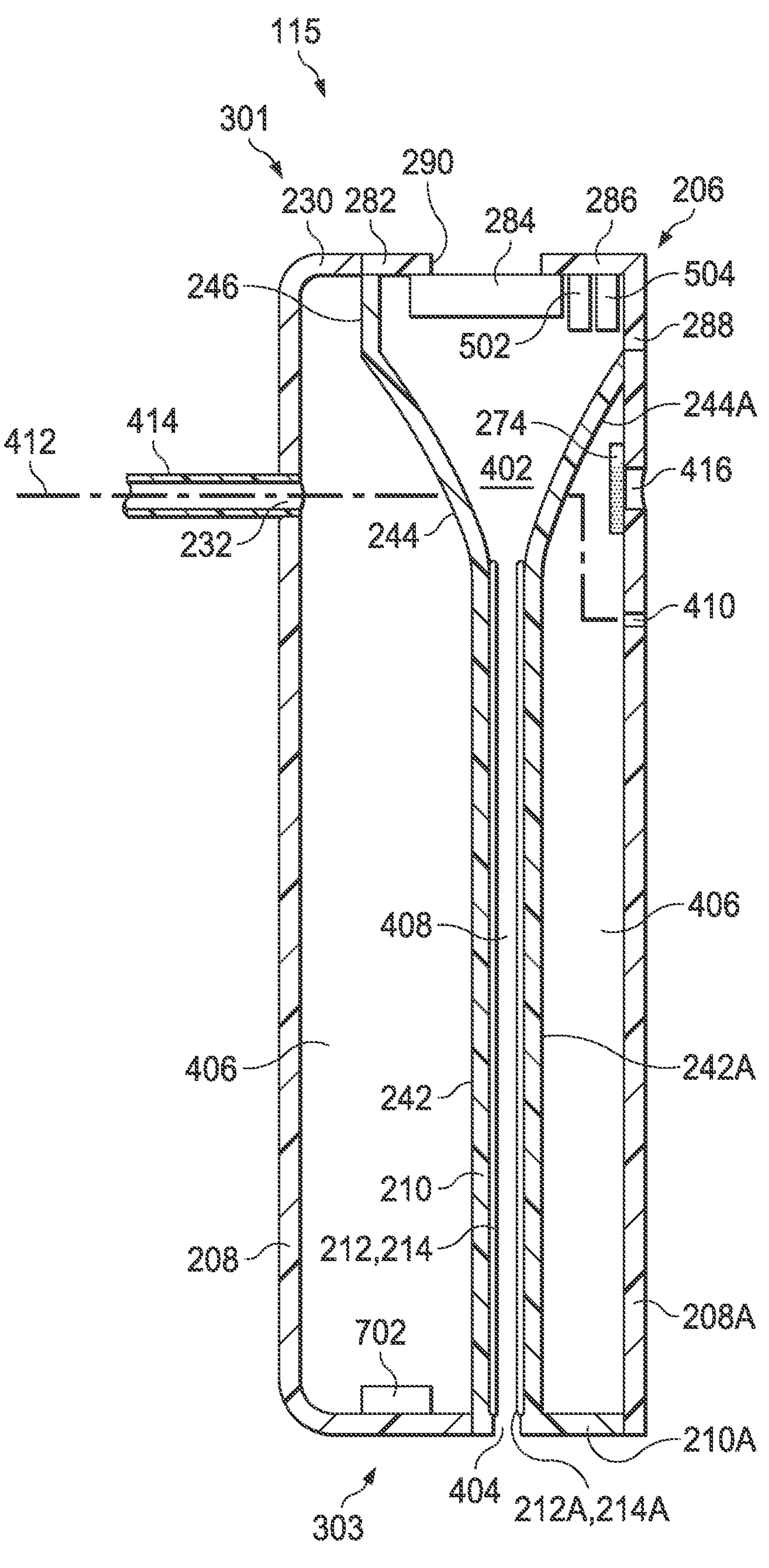
FIG. 7 is a cross-sectional view of the canister of FIG. 2 illustrating an example of a humidity sensor that may be used with some embodiments.

FIG. 7 is a cross sectional view illustrating additional details that may be associated with some embodiments of the canister 115. In some embodiments, the canister 115 may further comprise a humidity sensor 702. The humidity sensor 702 may be located inside the first canister section 202. In other embodiments, the humidity sensor 702 may be located in the second canister section 204 or in a different location of the first canister section 202. The humidity sensor 702 may be coupled to the second side of the first outer section 208 near an end opposite the end 230.

The humidity sensor 702 may be configured to sense a humidity level in the canister 115. The humidity level that is detected may indicate the presence of fluid in the fluid chamber 406 of the canister 115. In some embodiments, the humidity sensor 702 may be configured to control the operation of the forced air device 284. For example, the forced air device 284 may be operated if the humidity sensor 702 senses a predetermined humidity level or a threshold humidity level in the fluid chamber 406 of the canister 115. The predetermined humidity level may be about 50% relative humidity to about 100% relative humidity. In other embodiments, the predetermined humidity level may be anything above ambient relative humidity. During operation, the humidity sensor 702 may detect the humidity level in the fluid chamber 406. In response, the humidity sensor 702 may generate and communicate a signal to the control board 504, which may operate the forced air device 284. If the humidity level decreases, the humidity sensor 702 may generate a signal indicative of the change in humidity level. In some embodiments, if the humidity sensor 702 senses that the humidity level is below the predetermined humidity level, the control board 504 may turn off the forced air device 284. In other embodiments, if the humidity level falls below the predetermined humidity level for about 10 minutes, the control board 504 may operate the forced air device 284 for an additional 2 minutes to 15 minutes. After the additional about 2 minutes to about 15 minutes, the control board 504 may turn off the forced air device 284.

Figure 8:
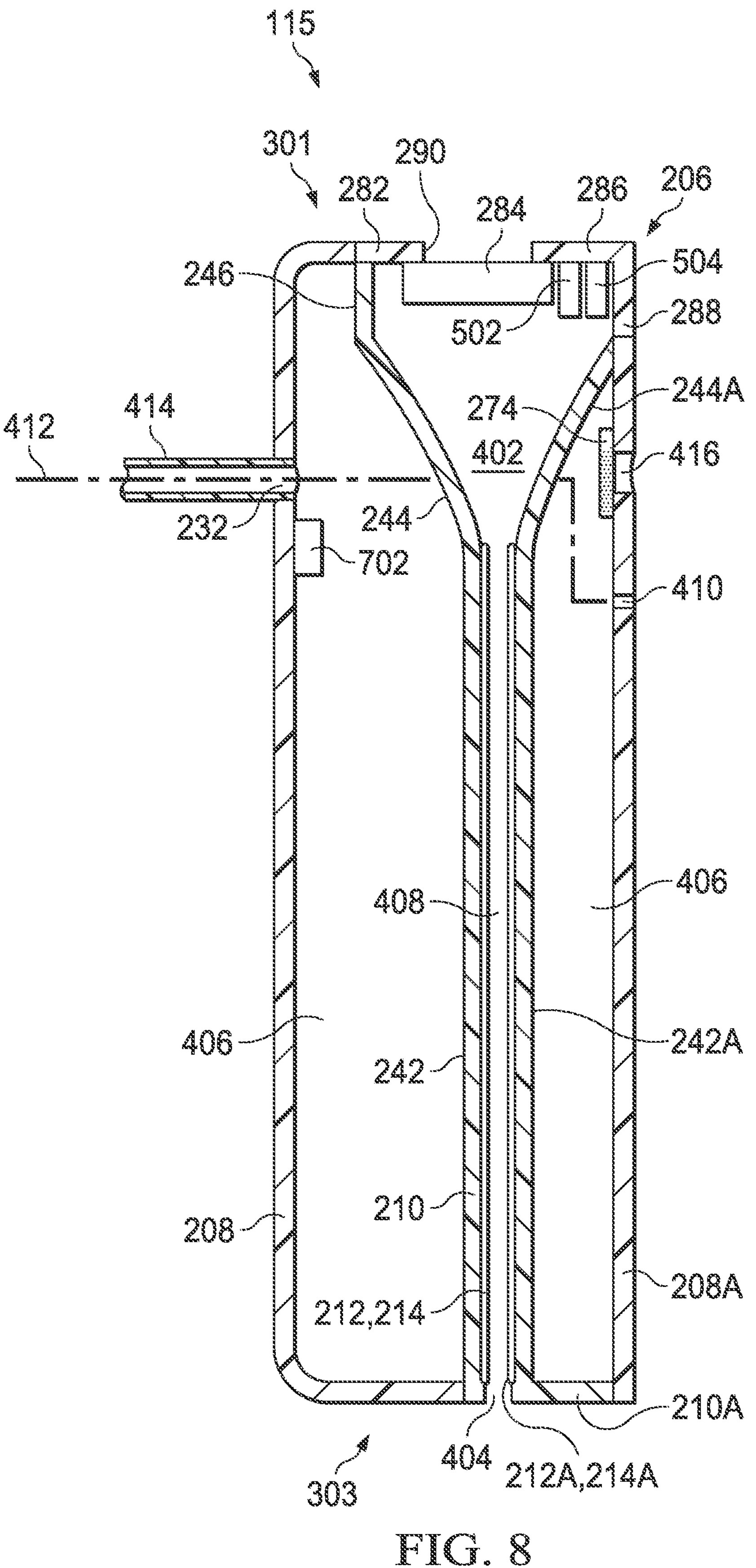
FIG. 8 is a cross-sectional view of another example embodiment of the canister of FIG. 2 having the humidity sensor disposed adjacent to a fluid removal path of the canister.

FIG. 8 is a cross sectional view illustrating additional details that may be associated with some embodiments of the canister 115. In some embodiments, the canister 115 may comprise the humidity sensor 702. The humidity sensor 702 may be located on the second side of the first outer section 208 adjacent to the fluid inlet 232. This location may allow the humidity sensor 702 to sense when fluid and exudate are entering the canister 115 from the dressing 110.

The humidity sensor 702 may be configured to sense the humidity level in the canister 115 which may indicate the presence of fluid in the fluid chamber 406 of the canister 115. In some embodiments, the humidity sensor 702 may be configured to control the operation of the forced air device 284. For example, the forced air device 284 may be operational if the humidity sensor 702 senses a predetermined humidity level in the fluid chamber 406 of the canister 115. In other embodiments, the forced air device 284 may be operational if the humidity sensor 702 senses that fluid is traveling through the fluid inlet 232 into the fluid chamber 406 of the canister 115. During operation, the humidity sensor 702 may detect the presence of fluid flowing into the fluid chamber 406 of the canister 115. In response, the humidity sensor 702 may generate and communicate a signal to the control board 504, which may operate the forced air device 284. If fluid stops flowing through the fluid inlet 232 into the fluid chamber 406, the humidity sensor 702 may generate a signal indicative of the change of the fluid flow into the fluid chamber 406. If there is no longer fluid flowing into the fluid chamber 406, the control board 504 may cease operating the forced air device 284. In other embodiments, if fluid has stopped flowing into the fluid chamber for about 10 minutes, the control board 504 may operate the forced air device 284 for an additional about 2 minutes to about 15 minutes. After the additional about 2 minutes to about 15 minutes, the control board 504 may turn off the forced air device 284.

Figure 9:
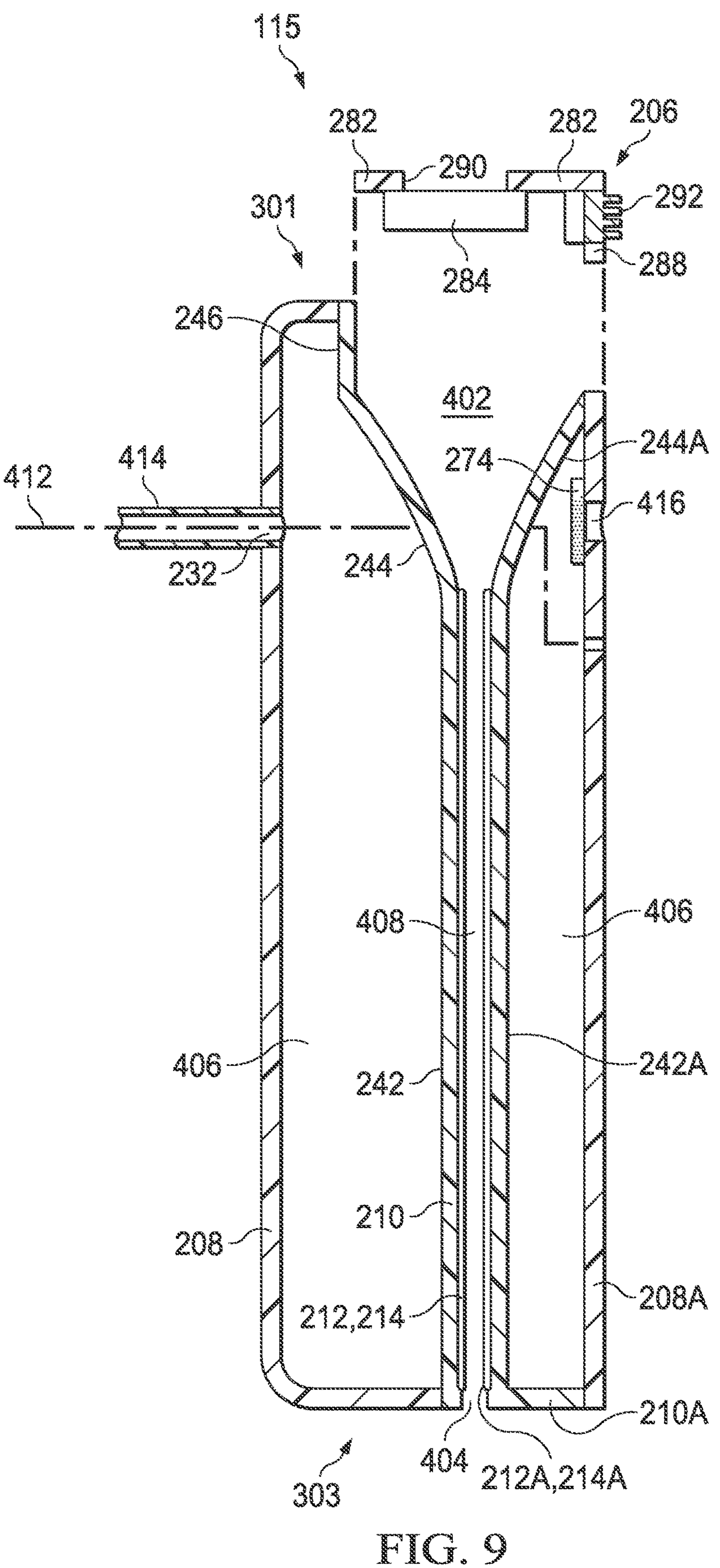
FIG. 9 is a cross-sectional view of the canister of FIG. 2 having a forced air module disconnected from the canister that may be associated with some embodiments.

FIG. 9 is the cross sectional view of the canister 115 of FIG. 4 having the forced air module 206 disconnected from the canister 115. The forced air module 206 may be disconnected from the canister 115 if the canister is full of fluid and ready for disposal. If the forced air module 206 is removed from the canister 115, the first opening 402 may be exposed. The canister 115 may remain a sealed space for any fluid located in the fluid chamber 406.

By disconnecting the forced air module 206 from the canister 115, the forced air module 206 may be disassembled to allow for appropriate disposal. The forced air module 206 may need to be disposed via Waste Electrical Electronic Equipment (WEEE) standards and the canister 115 may need to be disposed of via biohazard standards. By removing the forced air module 206 from the canister 115, health care providers may be able to minimize any complications when separating WEEE from biohazard waste. In some embodiments, the forced air module 206 may be designed so that the electric components such as electronic component 292 can be removed with ease from the other elements of the removable plate 282. This design may allow the electronic component 292 to be disposed of via WEEE while the forced air device 284 may be disposed of via biohazard waste.

Figure 10:
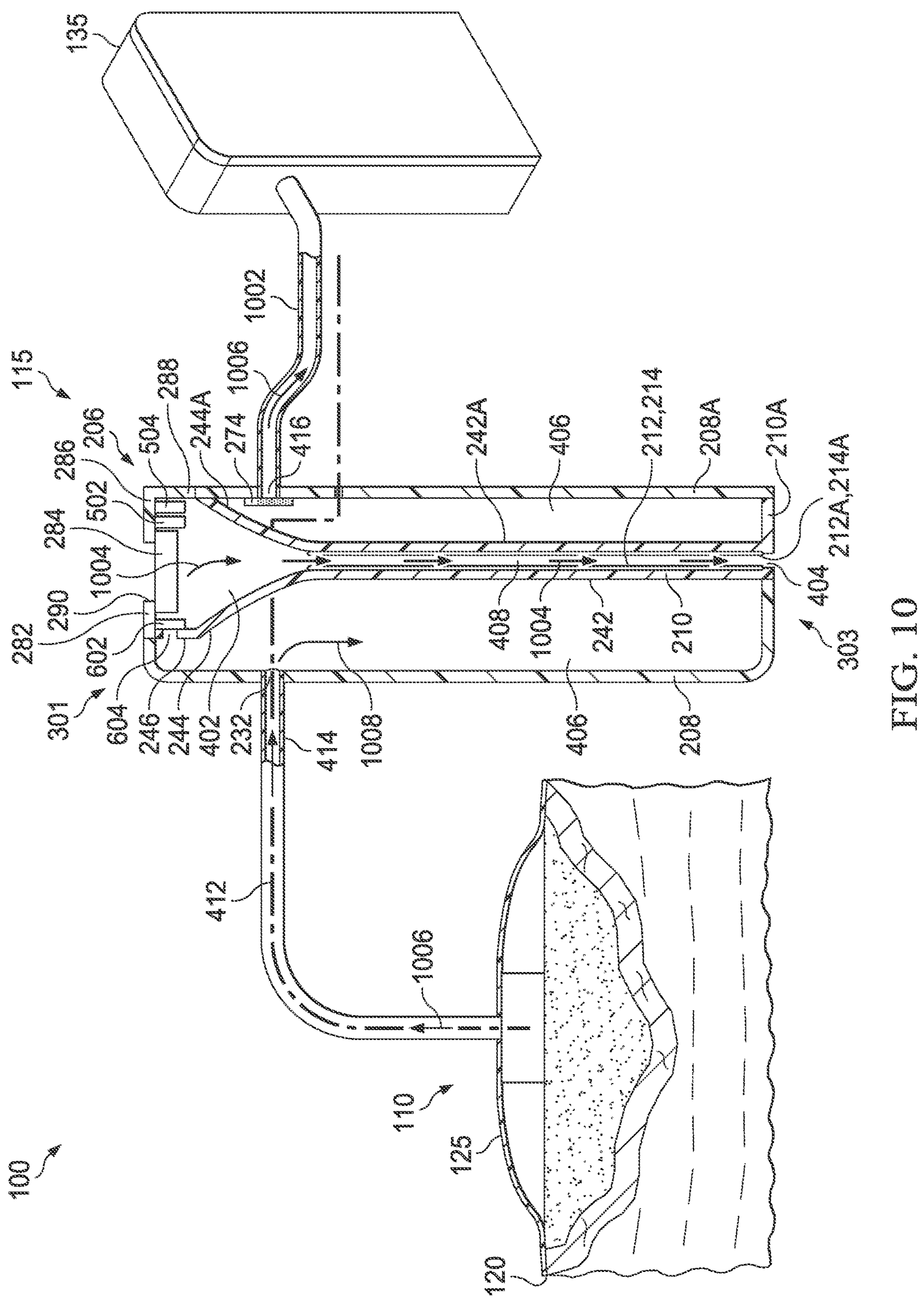
FIG. 10 is a schematic view of the canister of FIG. 2 illustrating an operative embodiment of the therapy system of FIG. 1.

FIG. 10 is a perspective view illustrating additional details that may be associated with some embodiments of the therapy system 100 of FIG. 1. The therapy unit 135 may be coupled to the canister 115 and may be indirectly coupled to the dressing 110. In some embodiments, the therapy unit 135 may include the negative-pressure source 105, the controller 130, the first sensor 133, and the second sensor 140. The therapy unit 135 may be coupled to the canister through a conduit 1002 and through the sensor pathway 412. The canister 115 may be coupled to the dressing through the conduit 414.

During operation of the therapy system 100, the pressure sensor 602 may detect negative pressure in the fluid chamber 406 of the canister 115. The pressure sensor 602 may generate and communicate a signal to the control board 504 which may operate the forced air device 284. In response, the forced air device 284 may generate a fluid flow 1004 that may be directed from the first opening 402, through the fluid flow pathway 408, and through the second opening 404 to the ambient environment.

Arrows 1006 illustrate negative-pressure application to the therapy system 100. Negative pressure may be applied from negative-pressure source 105. Arrows 1008 illustrate the path that fluid from the dressing 110 takes to the fluid chamber 406 of the canister 115. Fluid may flow from the dressing 110 through the conduit 414 and into the canister through fluid inlet 232. Once fluid is located in the canister 115, any liquids in the fluid may be unable to reach the therapy unit 135 because they cannot pass through the hydrophobic filter 274 that is covering the reduced pressure inlet 416.

While the forced air device 284 is operating, the fluid flow 1004 may assist in evaporation of liquids housed within the canister 115. Evaporated liquids from the canister may enter the fluid flow pathway 408 through the first evaporative layer 214 and the second evaporative layer 214A. The evaporated liquids may flow through the fluid flow pathway 408 to the second opening 404 and escape to the ambient environment. If the negative-pressure source 105 is turned off, the pressure sensor may sense that there is no longer negative pressure in the fluid chamber 406 of the canister 115 or that the negative pressure in the fluid chamber 406 has fallen below a predetermined value. The pressure sensor 602 may generate and communicate a signal to the forced air device 284 that the forced air device 284 may be turned off. In some embodiments, the forced air device 284 may operate for an additional 12 and 25 minutes after the pressure sensor 602 detects that the negative pressure in the fluid chamber 406 has fallen below a predetermined value.

The systems, apparatuses, and methods described herein may provide significant advantages. For example, using canisters 115 with on-board forced air devices 284 may result in fewer canister changes, reduced weight and size of therapy systems, lower costs of therapy, and a reduction in plastic waste which may lead to improved environmental considerations. The removable plate 282 with an attached forced air device 284 may be easily attached to existing canisters 115 and used with existing or modular therapy systems. For example, canisters 115 with on-board forced air devices 284 may allow existing negative-pressure therapy systems to be optimized with increased fluid handling capacity. This increased fluid handling capacity may lead to a reduction in waste and an increase in time that the canister 115 is able to be used before disposal.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the canister 115, or both may be separated from other components of the therapy system 100 for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A canister comprising:

a first section configured to be fluidly coupled to a dressing and to store fluid;

a second section configured to be fluidly coupled to a therapy unit and to store fluid;

a fluid flow pathway disposed between the first section and the second section;

a forced air module configured to generate a fluid flow through the fluid flow pathway; and a pressure sensor disposed within the fluid flow pathway, wherein the pressure sensor is configured to cover an opening in the fluid flow pathway to allow the pressure sensor to sense pressure in the canister and the pressure sensor is electrically coupled to the forced air module and is configured to control the forced air module based on a pressure sensed in the canister.

2. The canister of claim 1, further comprising a fluid port on the first section configured to fluidly couple the canister to the dressing.

3. The canister of claim 1, wherein the canister further comprises a humidity sensor disposed within the canister.

4. The canister of claim 3, wherein the humidity sensor is proximate to an end of the canister opposite the forced air module.

5. The canister of claim 3, wherein a humidity sensor is coupled to the first section adjacent to a fluid connection point.

6. The canister of claim 1, wherein the first section and the second section comprise a clear rigid plastic.

7. The canister of claim 1, wherein each of the first section and the second section comprises an evaporative membrane, the fluid flow pathway disposed between the evaporative membrane of the first section and the evaporative membrane of the second section.

8. The canister of claim 7, the forced air module comprising:

a removable plate with an interior side and an exterior side; and a forced air device coupled to the interior side of the removable plate, the forced air device configured to direct a fluid flow through the fluid flow pathway.

9. The canister of claim 8, the forced air module further comprising a power source, the power source attached to the interior side of the removable plate and adjacent to the forced air device.

10. The canister of claim 9, the forced air module further comprising a control board, the control board attached to the interior side of the removable plate and adjacent to the power source.

11. The canister of claim 10, the forced air module further comprising a power control, the power control configured to extend through the removable plate from the exterior side to the interior side.

12. The canister of claim 11, wherein the power control is configured to provide communication between a user and the control board, the power control further configured to allow the user to start and stop the forced air device.

13. The canister of claim 8, the forced air module further comprising a heating device adjacent to the forced air device, the heating device configured to warm the fluid flow of the forced air device.

14. The canister of claim 13, wherein the fluid flow is heated to about 38 degrees C.

15. The canister of claim 1, further comprising a third canister section and a second fluid flow pathway disposed between the second section and the third canister section, the forced air module being further configured to generate a second fluid flow through the second fluid flow pathway.

16. A therapy system comprising:
a dressing configured to be positioned adjacent to a tissue site;
a canister comprising:
a first section comprising:
a first outer wall;
a first interior wall comprising a first side and a second side, the first interior wall configured to be attached to the first outer wall; and
a first evaporative membrane coupled to the second side of the first interior wall;
a second section comprising:
a second outer wall;
a second interior wall comprising a first side and a second side, the second interior wall configured to be attached to the second outer wall; and
a second evaporative membrane coupled to the first side of the second interior wall;
a fluid flow pathway disposed between the second side of the first interior wall and the first side of the second interior wall, the fluid flow pathway comprising:
a first opening on a first end of the canister; and
a second opening on a second end of the canister;
a forced air module configured to cover the first opening, the forced air module comprising:
a removable plate with an interior side and an exterior side; and
a forced air device coupled to the interior side of the removable plate, the forced air device configured to direct a fluid flow through the fluid flow pathway to the second opening; and
a pressure sensor disposed within the fluid flow pathway, wherein the pressure sensor is configured to cover an opening in the fluid flow pathway to allow the pressure sensor to sense pressure in the canister and the pressure sensor is electrically coupled to the forced air module and is configured to control the forced air module based on a pressure sensed in the canister; and
a therapy module comprising:
a negative pressure pump;
a control board electrically coupled to the negative pressure pump and the canister; and
a power source electrically coupled to the control board.

17. A method for fluid evaporation comprising:
positioning a dressing adjacent to a tissue site;
coupling a canister to the dressing, the canister comprising:
a first section comprising:
a first outer wall;
a first interior wall comprising a first side and a second side, the first interior wall configured to be attached to the first outer wall; and
a first evaporative membrane coupled to the second side of the first interior wall;
a second section comprising:
a second outer wall;
a second interior wall comprising a first side and a second side, the second interior wall configured to be attached to the second outer wall; and
a second evaporative membrane coupled to the first side of the second interior wall;
a fluid flow pathway disposed between the second side of the first interior wall and the first side of the second interior wall, the fluid flow pathway comprising:
a first opening on a first end of the canister; and
a second opening on a second end of the canister;
a forced air module configured to cover the first opening, the forced air module comprising:
a removable plate with an interior side and an exterior side; and
a forced air device coupled to the interior side of the removable plate, the forced air device configured to direct a fluid flow through the fluid flow pathway to the second opening; and
a pressure sensor disposed within the fluid flow pathway, wherein the pressure sensor is configured to cover an opening in the fluid flow pathway to allow the pressure sensor to sense pressure in the canister and the pressure sensor is electrically coupled to the forced air module and is configured to control the forced air module based on a pressure sensed in the canister;
connecting the canister and the dressing to a therapy module, the therapy module comprising:
a power source;
a negative pressure pump; and
a control board;
operating the negative pressure pump, the negative pressure pump configured to draw the tissue site to a therapy pressure and draw fluids away from the tissue site;
collecting fluids from the tissue site in the canister; and
operating the forced air module, wherein operating the forced air module comprises:
operating the forced air device, the forced air device configured to direct a fluid flow through the fluid flow pathway and over the first evaporative membrane and the second evaporative membrane; and
utilizing the first evaporative membrane and the second evaporative membrane to evaporate fluids from the canister to increase fluid handling capacity of the canister.

* * * * *